US012648777B2

(12) United States Patent
Kellar et al.

(10) Patent No.: US 12,648,777 B2
(45) Date of Patent: Jun. 9, 2026

(54) KNEE JIG POSITIONING APPARATUS

(71) Applicant: Little Engine, LLC, Belmont, NC (US)

(72) Inventors: Franz W. Kellar, Gastonia, NC (US); Harold L. Crowder, Concord, NC (US); Franz Austen Kellar, Gastonia, NC (US)

(73) Assignee: DYNAMIC BALANCER SYSTEMS LLC, Belmont, NC (US)

( * ) Notice: Subject to any disclaimer, the term of this patent is extended or adjusted under 35 U.S.C. 154(b) by 51 days.

(21) Appl. No.: 18/496,083

(22) Filed: Oct. 27, 2023

(65) Prior Publication Data

US 2024/0197338 A1 Jun. 20, 2024

Related U.S. Application Data

(62) Division of application No. 18/068,948, filed on Dec. 20, 2022, now Pat. No. 11,826,057.

(51) Int. Cl.
| | |
|---|---|
| *A61B 17/15* | (2006.01) |
| *A61B 17/17* | (2006.01) |
| *A61B 34/20* | (2016.01) |

(52) U.S. Cl.
CPC ........ *A61B 17/157* (2013.01); *A61B 17/1764* (2013.01); *A61B 34/20* (2016.02); *A61B 2034/2046* (2016.02)

(58) Field of Classification Search
CPC ................................ A61F 17/15; A61F 17/154
See application file for complete search history.

(56) References Cited

U.S. PATENT DOCUMENTS

| | | | |
|---|---|---|---|
| 1,100,382 | A | 6/1914 | Levison |
| 4,124,026 | A | 11/1978 | Berner et al. |
| | | (Continued) | |

FOREIGN PATENT DOCUMENTS

| | | |
|---|---|---|
| WO | 2014188184 | 11/2014 |
| WO | 2017195046 | 11/2017 |

OTHER PUBLICATIONS

Attune Knee System, CAS Surgical Technique, Published 2014, accessed at "http://synthes.vo.llnwd.net/o16/LLNWMB8/US%20Mobile/Synthes%20North%20America/Product%20Support%20Materials/Technique%20Guides/DSUS-JRC-0514-0141%20ATTUNE_CAS_ST.pdf".

(Continued)

*Primary Examiner* — Andrew Yang
(74) *Attorney, Agent, or Firm* — Shumaker, Loop & Kendrick LLP

(57) ABSTRACT
An apparatus for securing and positioning a jig on a human joint includes: a mounting bracket; a first tracking marker coupled to the mounting bracket, configured to generate a first signal representative of the position and orientation in space of the mounting bracket; a mounting head coupled to a distal end of the mounting bracket by an adjustment mechanism configured to permit six degree of freedom of movement of the mounting head relative to the mounting bracket; position feedback means configured to generate a second signal representative of the position and orientation of the mounting head relative to the mounting bracket; a mounting element coupled to the mounting bracket; an electronic receiving device configured to receive the first and second signals; and a display configured to display the position and orientation of the mounting head relative to the mounting bracket.

11 Claims, 28 Drawing Sheets

(56)     References Cited

U.S. PATENT DOCUMENTS

| | | | |
|---|---|---|---|
| 5,713,897 | A | 2/1998 | Goble et al. |
| 5,935,129 | A | 8/1999 | McDevitt et al. |
| 6,022,377 | A | 2/2000 | Nuelle et al. |
| 6,080,154 | A | 6/2000 | Reay-Young et al. |
| 6,162,234 | A | 12/2000 | Freedland et al. |
| 6,205,411 | B1 | 3/2001 | DiGioia, III et al. |
| 6,859,661 | B2 | 2/2005 | Tuke |
| 7,070,598 | B2 | 7/2006 | Lim et al. |
| 7,849,751 | B2 | 12/2010 | Clark et al. |
| 9,585,615 | B2 | 3/2017 | Singh et al. |
| 10,076,377 | B2 | 9/2018 | Bonutti et al. |
| 10,405,849 | B1 | 9/2019 | Cole et al. |
| 10,478,171 | B1 | 11/2019 | Cole et al. |
| 10,555,729 | B1 | 2/2020 | Cole et al. |
| 11,602,443 | B1 | 3/2023 | Cole et al. |
| 11,642,148 | B2 | 5/2023 | Ujihira |
| 2001/0008971 | A1 | 7/2001 | Schwartz et al. |
| 2003/0032983 | A1 | 2/2003 | Bonutti et al. |
| 2004/0064191 | A1 | 4/2004 | Wasielewski |
| 2005/0222488 | A1 | 10/2005 | Chang et al. |
| 2005/0267485 | A1 | 12/2005 | Cordes et al. |
| 2006/0235290 | A1* | 10/2006 | Gabriel ................. A61B 34/20 600/407 |
| 2008/0051798 | A1 | 2/2008 | Colquhoun et al. |
| 2008/0114367 | A1 | 5/2008 | Meyer |
| 2008/0288060 | A1 | 11/2008 | Kaye et al. |
| 2010/0007140 | A1 | 1/2010 | Duquette et al. |
| 2010/0249659 | A1 | 9/2010 | Sherman et al. |
| 2010/0250571 | A1 | 9/2010 | Pierce et al. |
| 2010/0256612 | A1 | 10/2010 | Dell'Oca |
| 2011/0093081 | A1 | 4/2011 | Chana et al. |
| 2012/0095515 | A1 | 4/2012 | Hamilton |
| 2013/0102929 | A1 | 4/2013 | Haight et al. |
| 2013/0131737 | A1 | 5/2013 | Cheng et al. |
| 2013/0226189 | A1 | 8/2013 | Young |
| 2013/0261502 | A1 | 10/2013 | Sherman |
| 2014/0025081 | A1 | 1/2014 | Lorio et al. |
| 2014/0094715 | A1 | 4/2014 | Stein et al. |
| 2014/0194907 | A1 | 7/2014 | Bonutti et al. |
| 2014/0257381 | A1 | 9/2014 | Palese |
| 2014/0277526 | A1 | 9/2014 | Stein et al. |
| 2014/0296979 | A1 | 10/2014 | Delfosse et al. |
| 2015/0105782 | A1 | 4/2015 | D'Lima et al. |
| 2016/0007909 | A1 | 1/2016 | Singh et al. |
| 2016/0030156 | A1 | 2/2016 | Cole |
| 2016/0106409 | A1 | 4/2016 | Moholkar |
| 2016/0278754 | A1 | 9/2016 | Todorov |
| 2016/0278944 | A1 | 9/2016 | D'Lima et al. |
| 2016/0287263 | A1* | 10/2016 | Firmbach ............. A61B 17/157 |
| 2016/0338751 | A1 | 11/2016 | Kellar et al. |
| 2017/0035409 | A1 | 2/2017 | Fallin et al. |
| 2017/0065438 | A1 | 3/2017 | Burnikel |
| 2017/0172624 | A1 | 6/2017 | Brunner et al. |
| 2017/0312099 | A1 | 11/2017 | Paziesnyek |
| 2018/0049622 | A1 | 2/2018 | Ryan et al. |
| 2018/0116278 | A1 | 5/2018 | Lang |
| 2018/0153599 | A1 | 6/2018 | Daly et al. |
| 2018/0177612 | A1 | 6/2018 | Masei et al. |
| 2018/0185100 | A1 | 7/2018 | Weinstein et al. |
| 2018/0199952 | A1 | 7/2018 | Cole |
| 2018/0296232 | A1 | 10/2018 | Nielsen et al. |
| 2019/0076273 | A1 | 3/2019 | Goodchild et al. |
| 2019/0167447 | A1 | 6/2019 | Angibaud |
| 2019/0183554 | A1 | 6/2019 | Pedicini |
| 2019/0224016 | A1 | 7/2019 | Walker et al. |
| 2019/0358056 | A1 | 11/2019 | Lerat et al. |
| 2020/0155135 | A1 | 5/2020 | Cole et al. |
| 2020/0237441 | A1 | 7/2020 | Zuhars et al. |
| 2022/0398744 | A1* | 12/2022 | Couture ................ A61B 34/20 |
| 2023/0390073 | A1 | 12/2023 | Kellar et al. |
| 2023/0390080 | A1 | 12/2023 | Cole et al. |

OTHER PUBLICATIONS

Bathis et al., "Flexion Gap Configuration in Total Knee Arthroplasty Following Hight Tibial Osteotomy", published online Sep. 30, 2004, International Orthopaedics (SICOT) 28: 366-369.

M. J. Winemaker, MDd, FRCS (C), "Perfect Balance in Total Knee Arthroplasty, The Elusive Compromise", The Journal of Arthroplasty vol. 17. No. 1 2002, 2002, Churchill Livingstone, Canada.

* cited by examiner

56B'

56A'

56B"

56A"

KNEE JIG POSITIONING APPARATUS

BACKGROUND

This invention relates generally to medical devices and instruments, and more particularly to a jig positioning apparatus for a knee joint and methods for its use.

Total knee arthroplasty ("TKA") is a procedure for treating an injured, diseased, or worn human knee joint. In a TKA, an endoprosthetic joint is implanted, replacing the bearing surfaces of the joint with artificial members. Proper alignment of the joint and substantially equal tension in the soft tissues surrounding the joint are important factors in producing a good surgical outcome.

A human knee joint "J" is shown in FIGS. 1-4. The joint J is prepared for implantation by cutting away portions of the femur "F" and the tibia "T". FIGS. 1 and 2 show the joint in extension, with cutting planes for a tibial cut 1 and a distal femoral cut 2. The tibial cut 1 and the distal femoral cut 2 cooperate to define an extension gap "EG". FIGS. 3 and 4 show the joint J in flexion, with a cutting plane 3 shown for a posterior cut. The tibial cut 1 and the posterior cut 3 cooperate to define a flexion gap "FG".

FIG. 5 depicts an exemplary endoprosthesis 10 (i.e., implant) of a known type. The endoprosthesis 10 includes a tibial component 12 and a femoral component 14. The tibial component 12 is made up of a tibial tray 16 and an insert 18. The insert 18 has a back surface 20 which abuts the tibial tray 16 and an opposed articular surface 22. The tray includes a prominent keel 24 protruding in the inferior direction (i.e. down a longitudinal axis of the tibia). The tibial tray 16 may be made from a hard, wear-resistant material such as a biocompatible metal alloy. The insert 18 may be made from a low-friction material such as a bio-compatible plastic.

The femoral component 14 includes a back surface 28 shaped to abut a surface of the femur F that has been appropriately shaped and an articular surface 30 comprising medial and lateral condyles 32 and 34, respectively. The femoral component 14 may be made from a hard, wear-resistant material such as a biocompatible metal alloy.

The back surface 28 includes multiple faces collectively defining a rough "U" or "J" shape. The back surface 28 includes protruding locator pins 36.

The tibial tray 16 is implanted into the tibia T and the femoral component 14 is implanted into the femur F. The insert 18 is placed into the tibial tray 16. The articular surface 22 of the insert 18 bears against the articular surface 30 of the femoral component 14, defining a functional joint.

In the illustrated example, the endoprosthesis 10 is of the cruciate-retaining ("CR") type. It includes a cutout or notch 38 in the posterior aspect of the tibial component 12 which provides a space for the posterior cruciate ligament ("PCL").

A goal of total knee arthroplasty is to obtain symmetric and balanced flexion and extension gaps FG, EG (in other words, two congruent rectangles). These gaps are generally measured in millimeters of separation, are further characterized by a varus or valgus angle measured in degrees, and are measured after the tibia cut, distal femoral cut, and posterior femoral cut have been done (to create flat surfaces from which to measure). It follows that, to achieve this balance, the ligament tension in the lateral and medial ligaments would be substantially equal on each side or have a surgeon-selected relationship, and in each position.

One problem with prior art arthroplasty techniques is that guiding the cutting tools used to make bone resections can require complex equipment.

BRIEF SUMMARY OF THE INVENTION

This problem is addressed by a jig positioning apparatus operable to an apparatus for securing and positioning a jig on a human joint and a method for its use.

According to one aspect of the technology described herein, an apparatus for securing and positioning a jig on a human joint includes: a mounting bracket; a first tracking marker coupled to the mounting bracket, configured to generate a first signal representative of the position and orientation in space of the mounting bracket; a mounting head coupled to a distal end of the mounting bracket by an adjustment mechanism configured to permit six degree of freedom of movement of the mounting head relative to the mounting bracket; position feedback means configured to generate a second signal representative of the position and orientation of the mounting head relative to the mounting bracket; a mounting element coupled to the mounting bracket; an electronic receiving device configured to receive the first and second signals; and a display configured to display the position and orientation of the mounting head relative to the mounting bracket.

BRIEF DESCRIPTION OF THE DRAWINGS

The invention may be best understood by reference to the following description taken in conjunction with the accompanying drawing figures in which.

DETAILED DESCRIPTION OF THE INVENTION

Figures 1, 2:
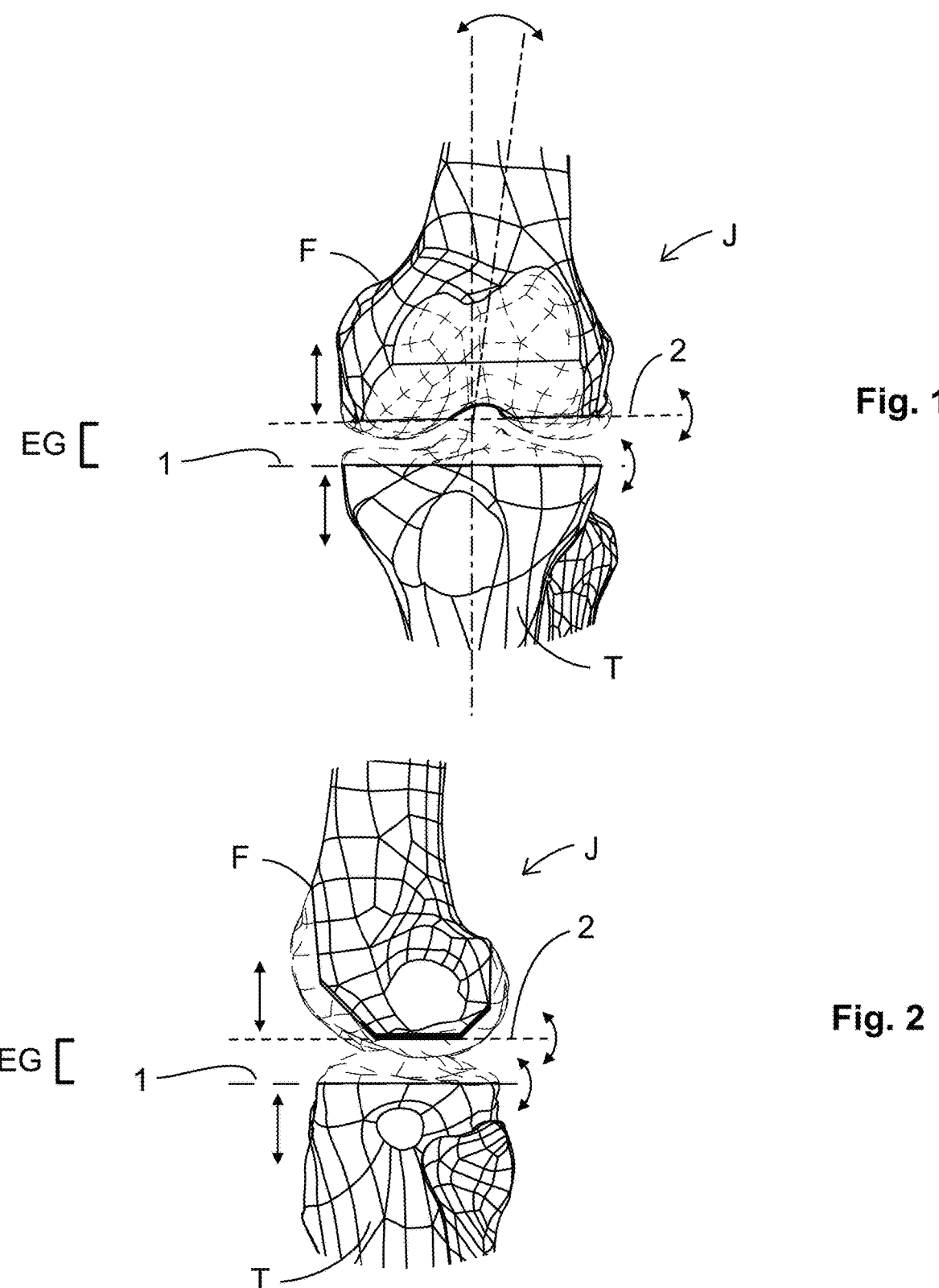
FIG. 1 is a view of the anterior aspect of the human knee joint in extension showing cutting planes for a total knee arthroplasty.
FIG. 2 is a view of the lateral aspect of the human knee joint of FIG. 1.
Figure 3:
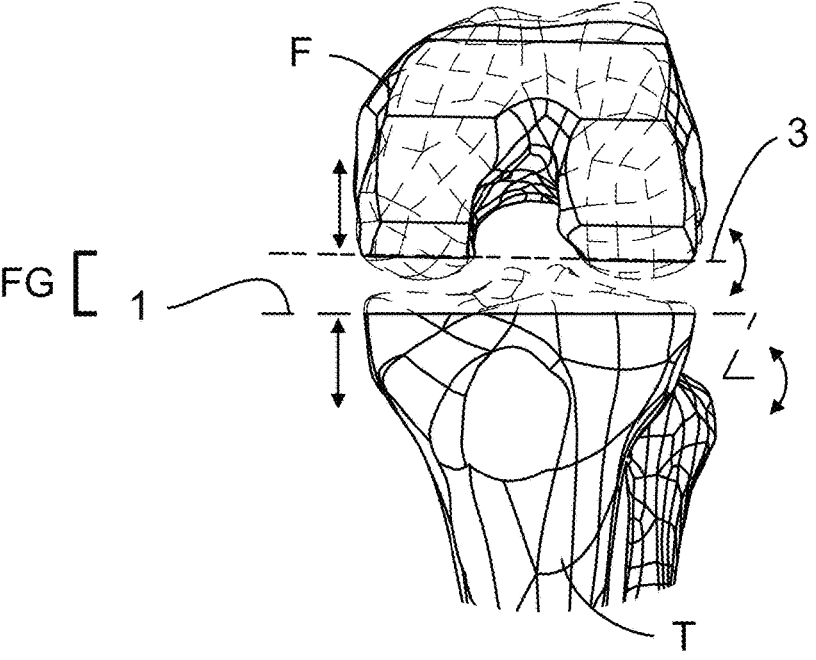
FIG. 3 is a view of the anterior aspect of the human knee joint in flexion showing cutting planes for a total knee arthroplasty.
Figure 4:
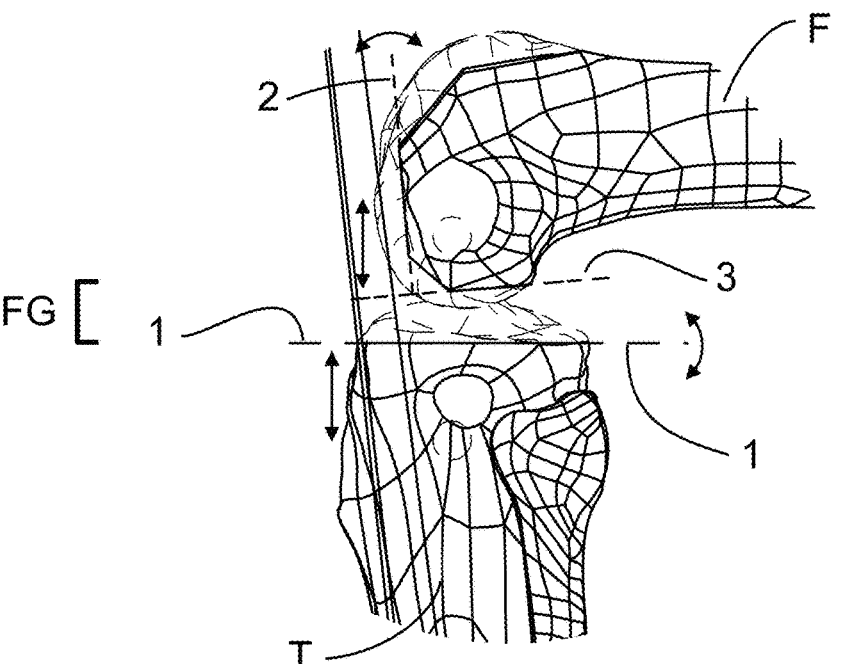
FIG. 4 is a view of the lateral aspect of the human knee joint of FIG. 3.
Figure 5:
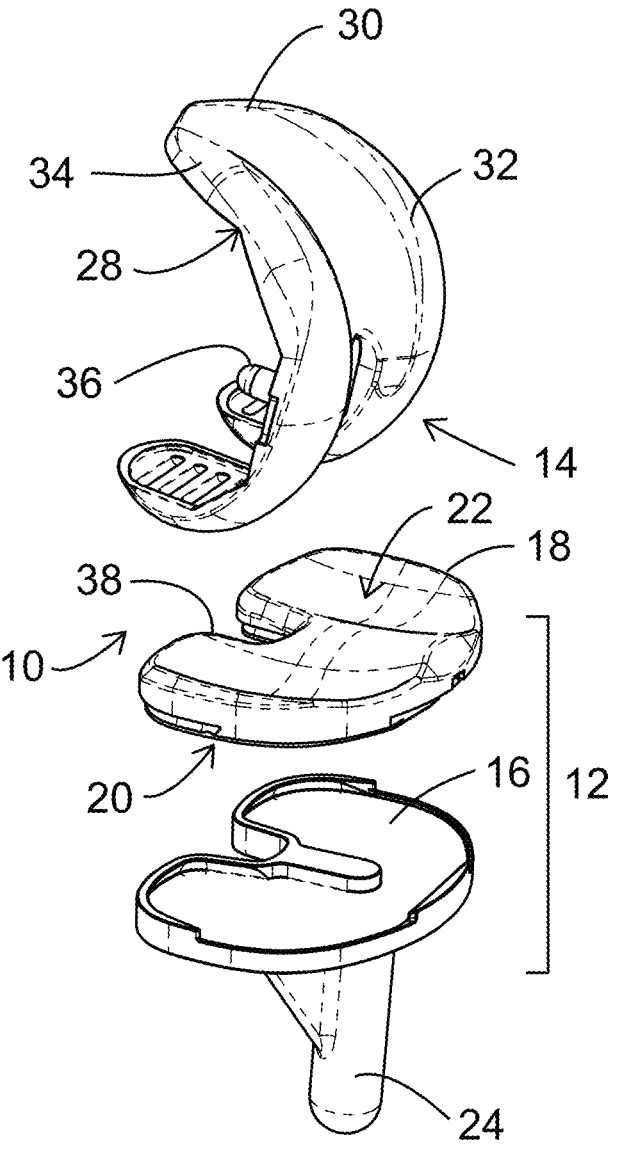
FIG. 5 is an exploded perspective view of a representative knee endoprosthesis.
Figure 6:
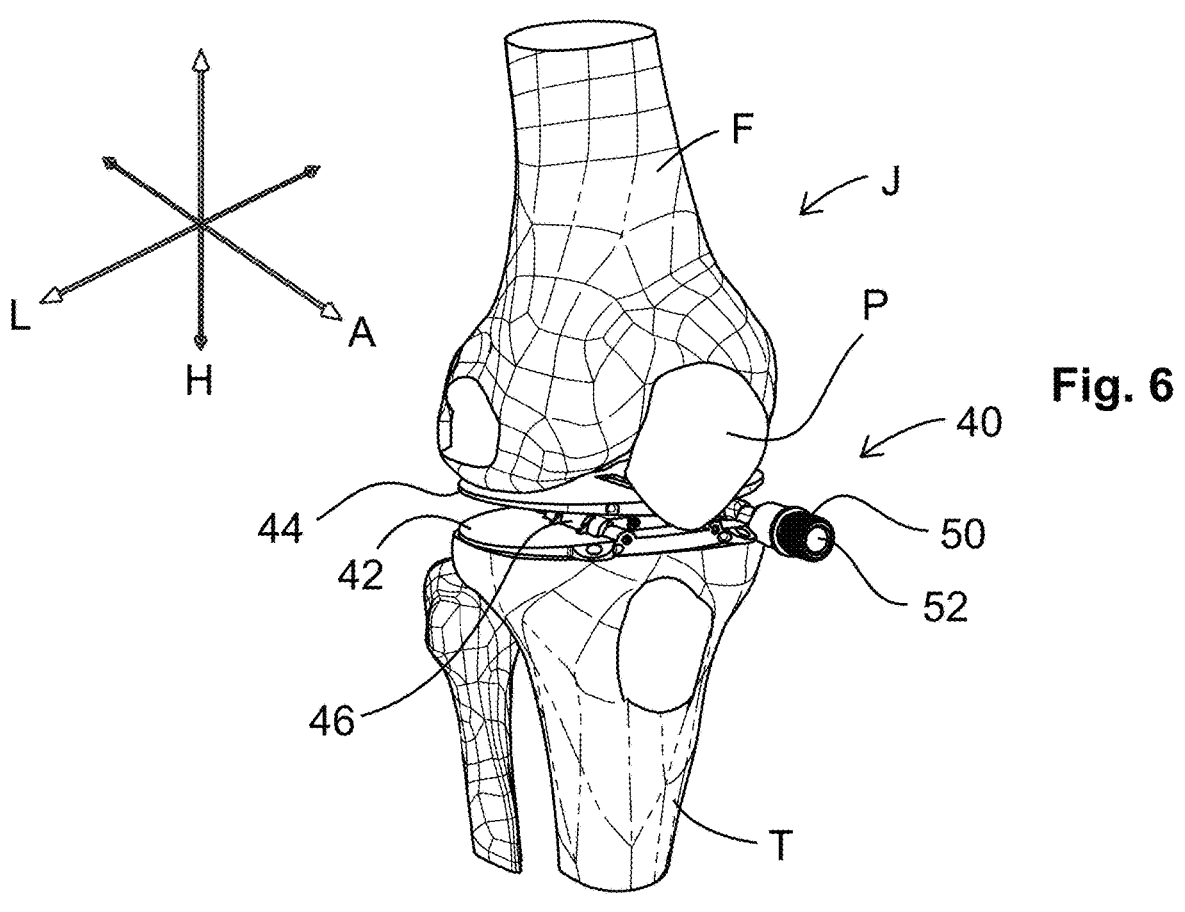
FIG. 6 is a perspective view of a human knee joint in an extended position, with a tensioner-balancer inserted therein.
Figure 7:
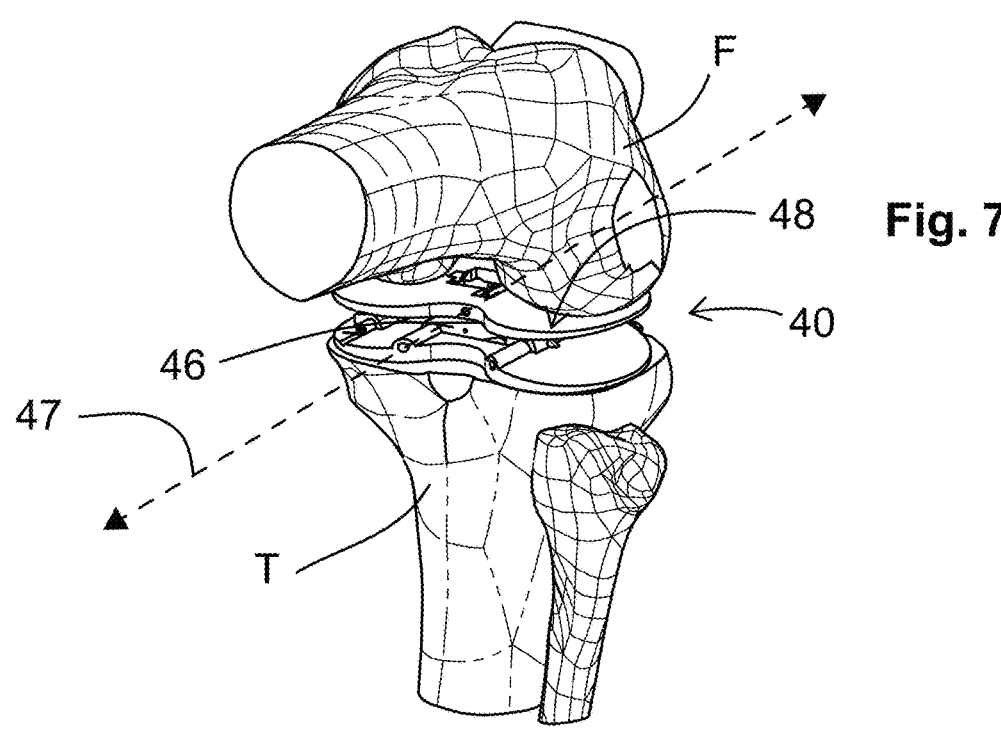
FIG. 7 is a view of the knee joint and tensioner-balancer of FIG. 6, in a flexed position.

Now, referring to the drawings wherein identical reference numerals denote the same elements throughout the various views, FIGS. 6 and 7 depict an exemplary embodiment of a tensioner-balancer 40 (alternatively referred to in various embodiments as a gap balancer, distractor, distractor-tensioner, or jack) which is useful for balancing a gap in a human knee joint as part of a total knee arthroplasty and for other therapeutic procedures. These views show the patella "P" in place.

Solely for purposes of convenient description, the tensioner-balancer 40 may be described as having a length extending along a lateral-to-medial direction "L", a width extending along an axial direction "A", and a height extending along a vertical direction "H", wherein the lateral direction, the axial direction, and the vertical direction are three mutually perpendicular directions. These directional terms, and similar terms such as "top", "bottom", "upper", "lower" are used merely for convenience in description and do not require a particular orientation of the structures described thereby.

In one aspect, the tensioner-balancer 40 may be described as having the ability to control the movement of one degree of freedom (e.g., translation along H) and measure the movement of a second degree of freedom (rotation about A) while constraining or fixing the remaining four degrees of freedom (translation along A and L; rotation about H and L).

The tensioner-balancer 40 comprises a baseplate 42 and a top plate 44 interconnected by a linkage 46. The linkage 46 and the tensioner-balancer 40 are movable between a retracted position in which the top plate 44 lies close to or against the baseplate 42, and an extended position in which the top plate 44 is spaced away from the baseplate 42. As described in more detail below, a means is provided to actuate the linkage 46 in response to an actuating force in order to separate the baseplate 42 and the top plate 44 in a controllable manner. This separation enables it to extend so as to apply a load to a knee joint. While the illustrated tensioner-balancer 40 includes a mechanically-operated linkage 46, it will be understood that this is just one operative example of a "distracting mechanism" operable to move the tensioner-balancer between retracted and extended positions. It is envisioned that the mechanical linkage could be replaced with other types of mechanical elements, or electrical, pneumatic, or hydraulic devices.

The top plate 44 includes a femoral interface surface 48 and is mounted to the linkage 46 in such a manner that it can freely pivot about pivot axis 47 (an axis corresponding to a varus/valgus angulation of the knee).

The baseplate 42 includes a tensioner-balancer coupler 50 having a first interface 52. In the illustrated example, the first interface 52 is configured as a socket. The coupler 50 is interconnected to the linkage such that an actuating force applied to the coupler 50, such as a torque, actuates the linkage 46.

Optionally, the tensioner-balancer 40 may incorporate means for measuring a force input. For example, the coupler 50 may incorporate a sensor (not shown) such as a strain gage operable to produce a signal representative of the torque applied to the coupler 50.

As a further option, the tensioner-balancer 40 may incorporate a separate measuring linkage (not shown) connected to the top plate and arranged to follow the movement of the top plate 44. The measuring linkage would be connected to a crank which would be in turn connected to an indicating shaft coaxial to the coupler. The measuring linkage may be arranged such that pivoting movement of the top plate results in rotation of the indicating shaft. The movement of the indicating shaft may be observed visually, or it may be detected by a sensor such as an RVDT or rotary encoder or resolver, which may be part of an instrument described below. This permits measurement of plate angle and/or vertical position.

The tensioner-balancer may be supplied with an appropriate combination of transducers to detect physical properties such as force, tilt angle, and/or applied load and generate a signal representative thereof. For example, the tensioner-balancer may be provided with sensors operable to detect the magnitude of extension (i.e. "gap height"), the angle of the top plate about the pivot axis 47 (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers.

Figure 8:
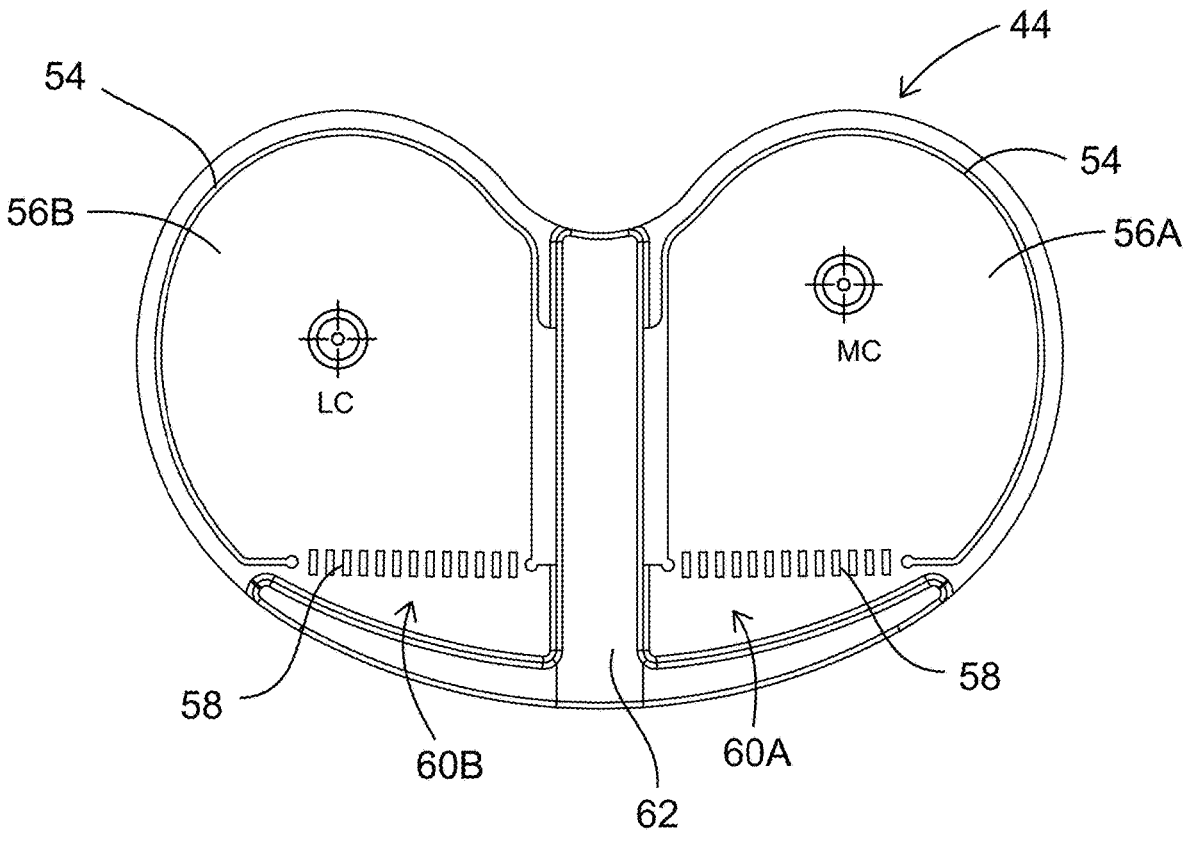
FIG. 8 is a top plan view of a top plate of the tensioner-balancer of FIG. 6.
Figure 9:
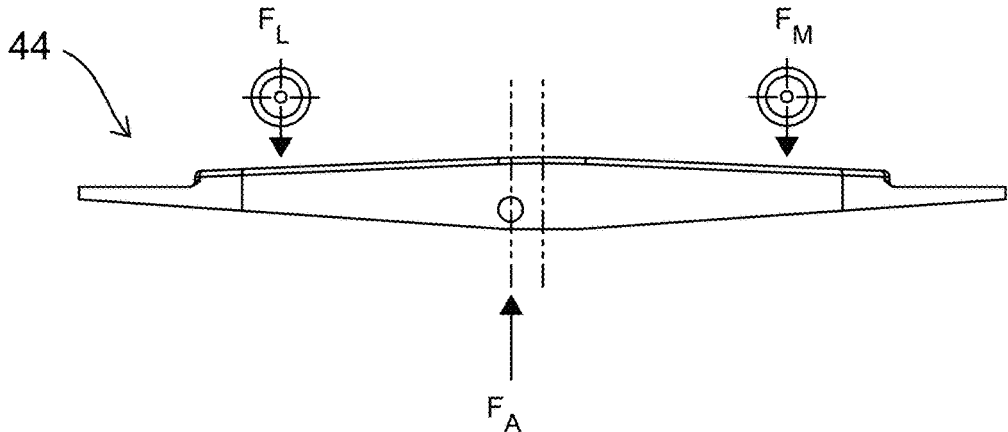
FIG. 9 is a front elevation view of the top plate of FIG. 8.

FIGS. 8 and 9 illustrate an exemplary configuration in which the top plate 44 includes grooves 54 which define medial and lateral cantilevered pads 56A, 56B respectively. Two or more spaced-apart strain gages 58 are mounted to the top plate 44 in a first left-right row 60A at the intersection between the medial pad 56A and the forward portion 62 of the top plate 44. Two or more spaced-apart strain gages 58 are mounted to the top plate 44 in a second fore-aft row 60B at the intersection between the lateral pad 56B and the forward portion 62 of the top plate 44.

Figure 10:
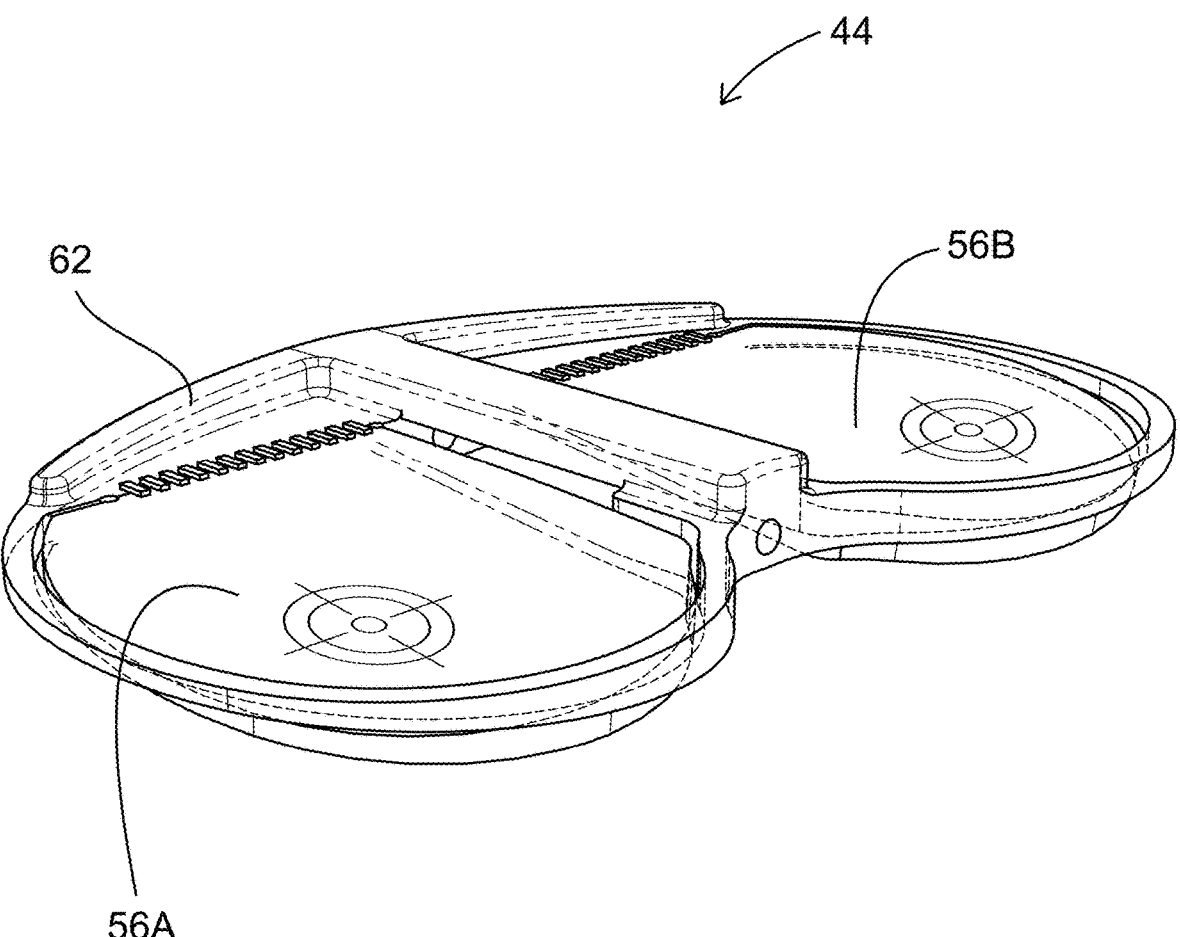
FIG. 10 is a perspective view of the top plate of FIG. 8, in a deflected position.

FIG. 10 shows the medial and lateral cantilevered pads 56A, 56B in a deflected position under load. The magnitude of deflection is greatly exaggerated for illustrative purposes.

Referring to FIG. 8, when the knee joint is articulated it is possible to identify an instantaneous point of peak contact pressure. There is one such point for each of the condyles. These positions are mapped onto the medial and lateral cantilevered pads 56A, 56B and labeled "MC" (standing for "medial load center") and "LC" (standing for "lateral load center").

Figure 11:
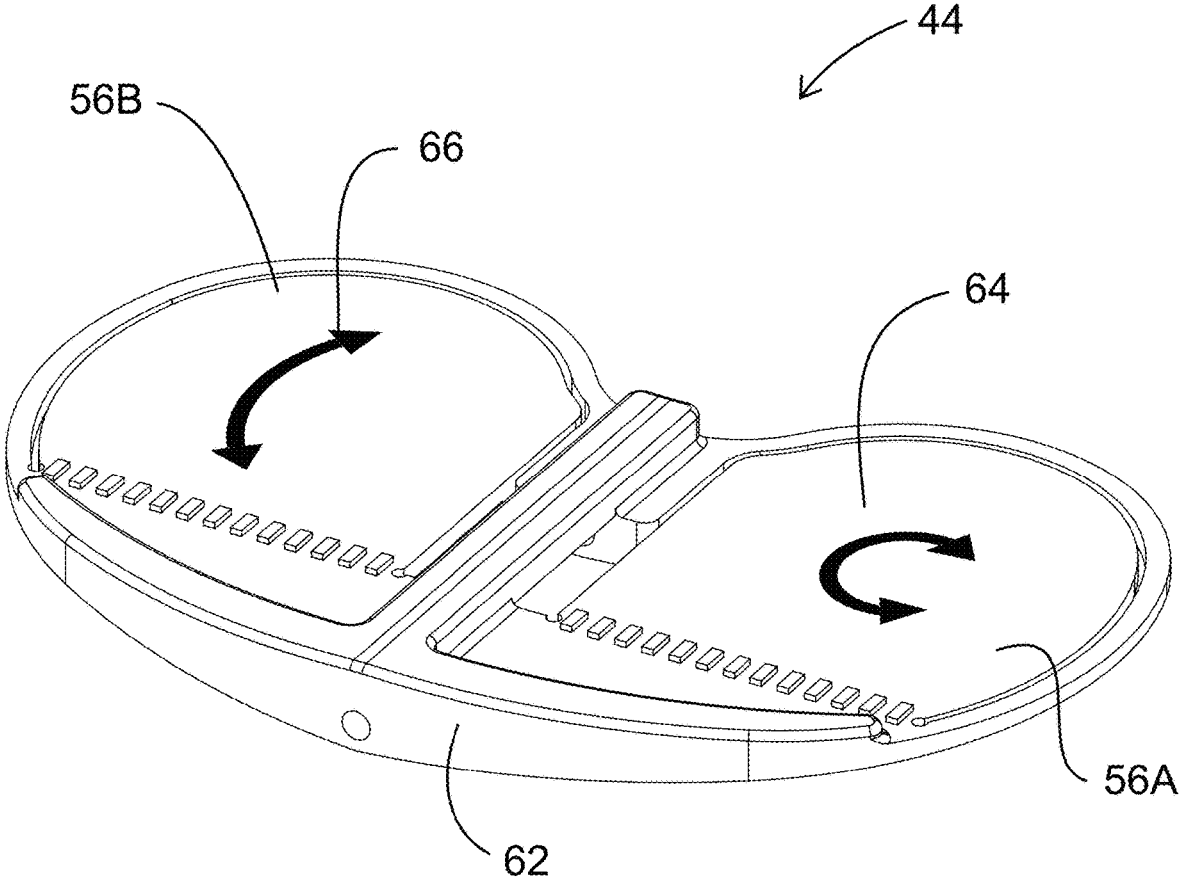
FIG. 11 is a perspective view of the top plate of FIG. 8, showing movement of contact points superimposed thereon.

Analysis by the inventors has shown that using the depicted configuration, with at least two spaced-apart strain gauges provided for each of the cantilevered pads 56A, 56B, it is possible to resolve the position of the load centers MC, LC in two axes. Stated another way, using this hardware, it is possible to identify the instantaneous lateral-medial and anterior-posterior position of the load centers LC, MC. Referring to FIG. 11, and as will be described further below, this enables the ability of the tensioner-balancer 40 to track certain relative movements of the femur F. One of these is referred to as "medial pivot" shown by arrow 64 and the other is referred to as "rollback", shown by arrow 66.

Figure 12:
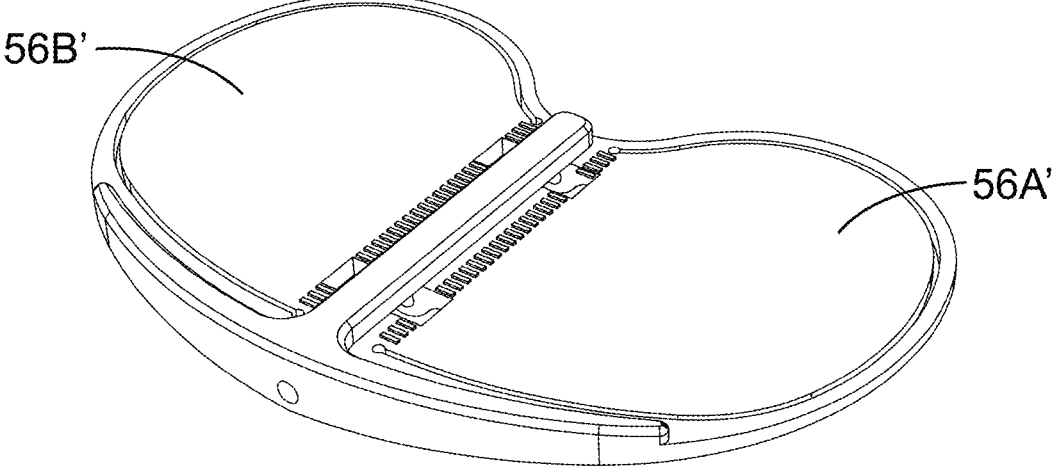
FIG. 12 is a perspective view of an alternative top plate configuration of the tensioner-balancer of FIG. 6.
Figure 13:
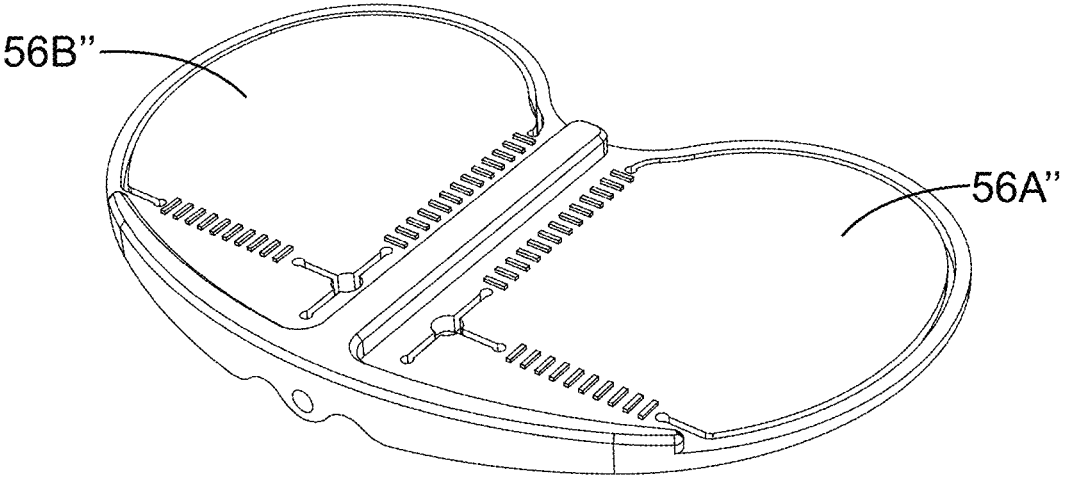
FIG. 13 is a perspective top plan view of an alternative top plate configuration of the tensioner-balancer of FIG. 6.

Various physical configurations of the top plate with cantilevered pads are possible with similar functionality. For example, FIG. 12 illustrates medial and lateral cantilevered pads 56A', 56B' which are cantilevered along an anterior-posterior axis (as opposed to a lateral-medial axis as shown in FIGS. 8-10). As another example, FIG. 13 illustrates medial and lateral cantilevered pads 56A", 56B" which are cantilevered along both an anterior-posterior axis and a lateral-medial axis. As another alternative (not separately illustrated), the lateral pad could be cantilevered along one axis and the medial pad could be cantilevered along a different axis.

Figure 14:
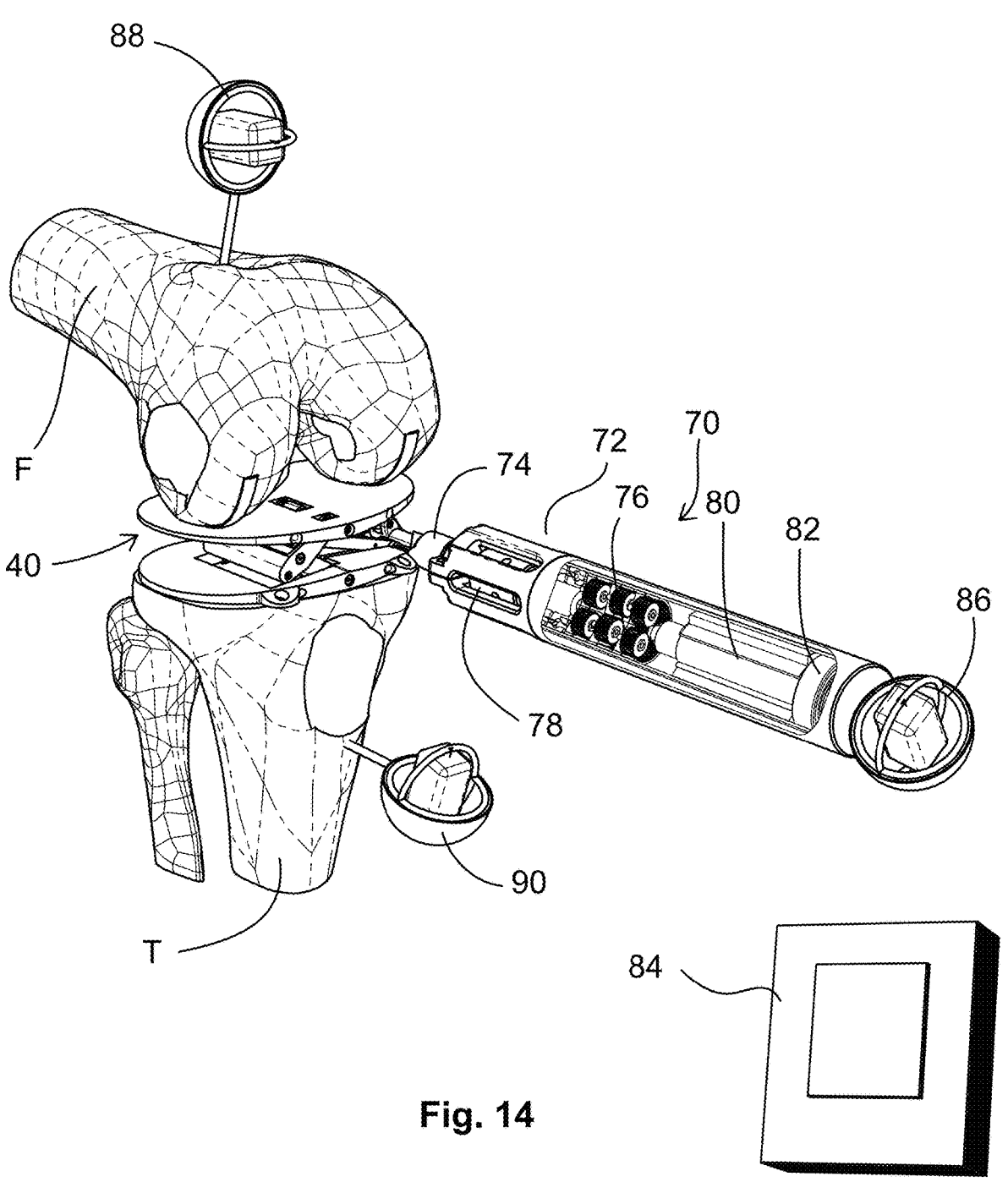
FIG. 14 is a perspective view of the human knee joint with a tensioner-balancer inserted therein and coupled to a instrument.

FIG. 14 illustrates an exemplary actuating instrument 70 for use with the tensioner-balancer 40. The actuating instrument 70 includes a barrel 72 with an instrument coupler 74 at its distal end defining a second interface (hidden in this view) which is complementary to the first interface 52 of the tensioner-balancer 40. The interior of barrel 72 includes an appropriate internal mechanism to apply torque to the instrument coupler 74 through a shaft 78, such as a stepper motor 80 with related control electronics including a rotary encoder coupled to a planetary gearset 76 that interconnects the stepper motor 80 and shaft 78.

The internal mechanism is operable to apply an actuating load to the tensioner-balancer 40. The actuating instrument 70 includes an electronic data transceiver, shown schematically at 82. The transceiver 82 may operate over a wired or wireless connection. The actuating instrument 70 may be supplied with an appropriate combination of transducers (not shown in FIG. 14) to detect physical properties such as force, tilt angle, and/or applied load and generate a signal representative thereof. For example, the tensioner-balancer 40 may be provided with sensors operable to detect the magnitude of extension (i.e. "gap height"), the angle of the top plate about the pivot axis (i.e. varus/valgus), and/or applied force in the extension direction. Nonlimiting examples of suitable transducers include strain gages, load cells, linear variable differential transformers ("LVDT"), rotary variable differential transformers ("RVDT"), or linear or rotary encoders or resolvers.

Displacement of the tensioner-balancer 40 may be derived from the encoder signals, knowing the kinematics of the linkage 46. The transceiver 82 is operable to transmit the signal.

A remote display 84 is configured to receive the signal and produce a display of the transducer data. As one example, the remote display 84 may be embodied in a conventional portable electronic device such as a "smart phone" or electronic tablet with suitable software programming. Optionally, the remote display 84 or other suitable transmitting device may be used to send remote operation commands to the actuating instrument 70.

In use, the remote display 84 permits the surgeon to observe the physical properties of the tensioner-balancer 40 in real time as the actuating instrument 70 is used to operate the tensioner-balancer 40.

Optionally, the actuating instrument 70 may incorporate a tracking marker 86. The tracking marker 86 is operable such that, using an appropriate receiving device, the position and orientation of the receiving device relative to the tracking marker 86 may be determined by receipt and analysis at the receiving device of signals transmitted by the tracking marker 86.

The function of the tracking marker is to provide six degree of freedom (6-DOF) position information in a local coordinate reference space (i.e., position and orientation in each of three mutually perpendicular axes). Some devices or systems may be able to provide 6-DOF position information without requiring line of sight for signals (e.g., electromagnetic spectrum energy). For example, as illustrated, the tracking marker 86 may be configured as an inertial navigation device including one or more accelerometers and gyroscopic elements capable of providing angular rate information and acceleration data in 3D space.

In an alternative embodiment which is not illustrated, the tracking marker may include one or more tracking points which may be configured as transmitting antennas, radiological markers, or other similar devices. This type of tracking marker may make use of line of sight transmission of signals to determine position.

Tracking markers 86 and appropriate receivers are known within the state-of-the-art.

A tracking marker 88 would be attached to the femur F in such a way that it has a substantially fixed position and orientation relative to the femur F. For example, a tracking marker 88 may be attached directly to the femur F.

In addition to the femur-mounted tracking marker 88, at least one additional tracking marker is provided which has a substantially fixed position and orientation relative to the tibia T. Where the actuating instrument 70 is rigidly coupled to the tensioner-balancer 40, the tibial tracking function may be provided by the tracking marker 86 of the actuating instrument 70. Alternatively, a tracking marker 90 may be attached directly to the tibia T.

Figures 15, 16:
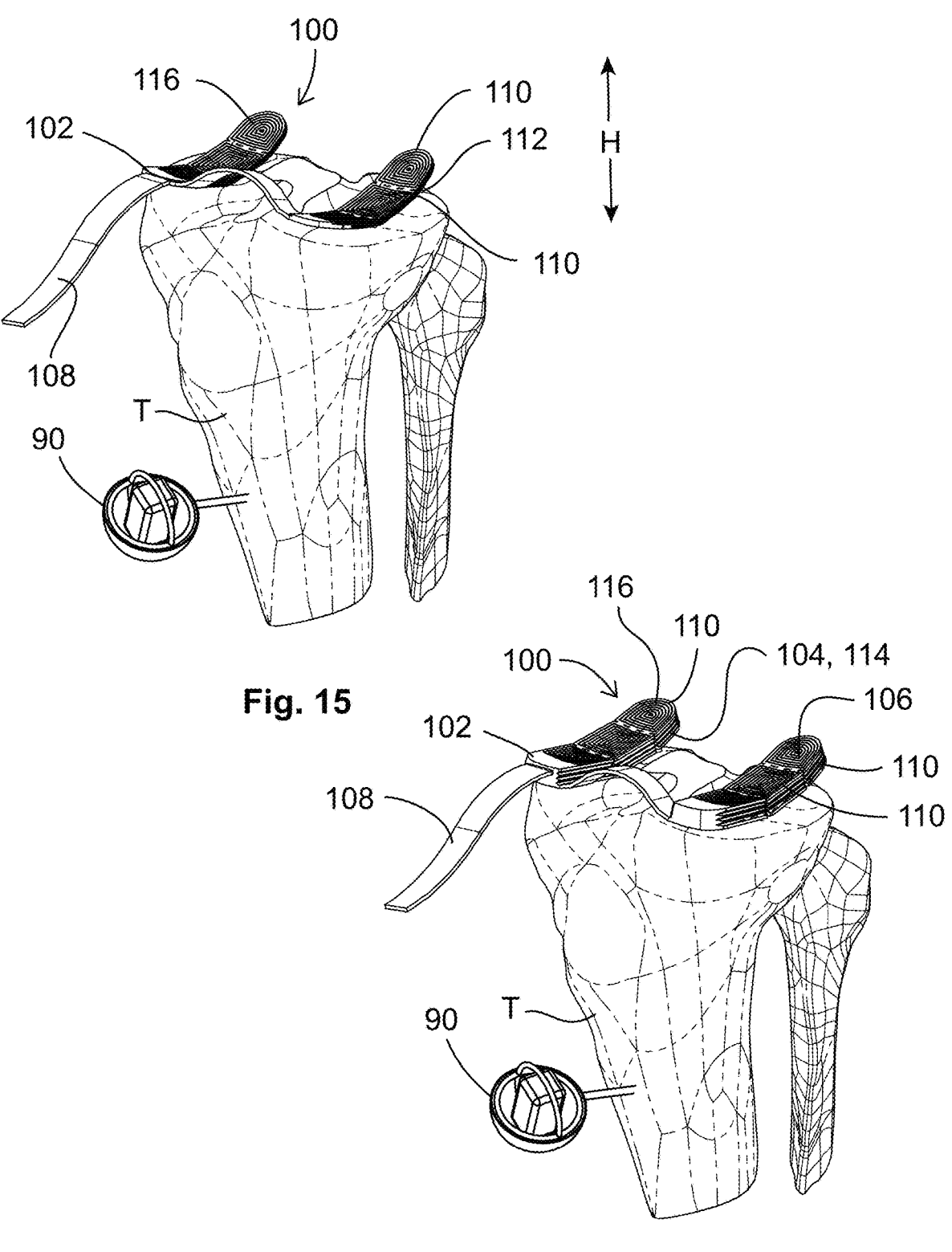
FIG. 15 is a perspective view of a tibia with an alternative tensioner-balancer disposed of thereon, in a retracted position.
FIG. 16 is a view of the tibia and tensioner-balancer of FIG. 15, in an extended position.

FIGS. 15 and 16 show another embodiment of a tensioner-balancer 100. The tensioner-balancer 100 comprises a body 102 with a tibial interface surface 104 and an opposed femoral interface surface 106. The tensioner-balancer 100 is generally U-shaped in plan form. It may include a coupler 108 providing electrical, fluid, and/or mechanical connections.

Generally, the overall thickness of the tensioner-balancer 100 (i.e., measured in direction H) may be on the order of one or two millimeters. This enables the tensioner-balancer 100 to be inserted into a knee joint J without first having to distract the joint or cut away any tissue.

The body 102 may be divided into a plurality of segments 110 which may be hinge elements 112 (e.g., live hinge strips) to allow the segments 110 to flex or pivot relative to each other. Each of the segments 110 may take the form of an expandable hollow chamber which may be inflated by fluid pressure or other means such as discrete electromechanical actuation, for example applying an electrical charge to a superelastic or memory metal. FIG. 15 shows the segments 110 in a deflated or retracted position. FIG. 16 shows the segments 110 in an inflated or extended position. The walls forming the segments 110 may be configured as an "accordion" or "corrugated" structure to permit them to selectively expand or collapse into a compact size.

An array of tibial force sensors 114 are attached to or integrated into the tibial interface surface 104. They may be arranged in a pattern such as a grid layout or a radial layout.

An array of femoral force sensors 116 are attached to or integrated into the femoral interface surface 106. They may be arranged in a pattern such as a grid layout or a radial layout.

Each of the force sensors 114, 116 includes one or more transducers operable to detect an applied force and produce a signal representative of (e.g., proportional to) the applied force and/or pressure. Optionally, each of the force sensors 114, 116 may detect and produce a signal representative of (e.g., proportional to) displacement and/or position (e.g., height). Nonlimiting examples of transducers effective to produce a signal include strain gauges, or miniature linear variable differential transformers (LVDT), or piezoelectric transducers. The force sensors are segmented into at least a 2D or two-axis array of sensor elements, e.g., a matrix which is addressable by X, Y reference, radial coordinates, or other suitable position location. The size of the individual sensor elements in the arrays may be selected as required to produce useful and actionable information.

The sensor arrays may be connected to an electronic receiving device as described elsewhere herein by a wired or wireless connection. Appropriate processors and software may be provided for interpretation of the signals from the sensor arrays.

Figure 17:
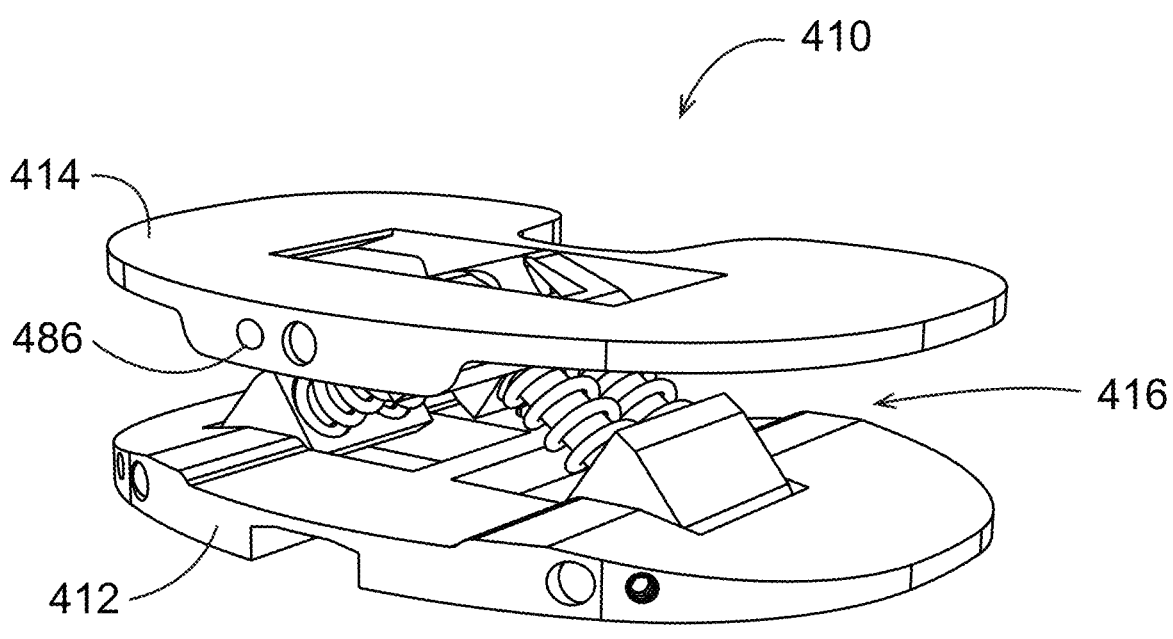
FIG. 17 is a perspective view of an alternative tensioner-balancer.
Figure 18:
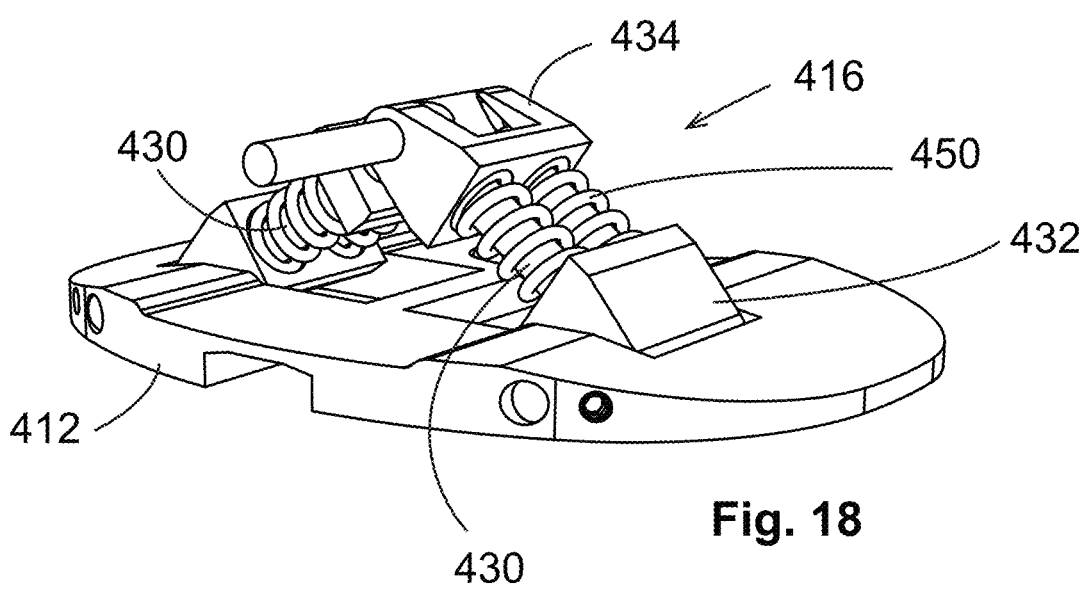
FIG. 18 is a perspective view of the tensioner-balancer of FIG. 17, with a top plate removed.

FIGS. 17 and 18 show another embodiment of a tensioner-balancer 410. The tensioner-balancer 410 includes a baseplate 412, top plate 414 defining a femoral interface surface, and a linkage 416. The linkage 416 is configured as a pair of links 430 each having a lower end 432 pivotally connected to the baseplate 412. Upper ends 434 of the links 430 are pivoted to each other and to the top plate 414. Each of the links 430 is a telescoping assembly and is provided with one or more springs 450 which are arranged so as to urge the linkage 416 towards an extended position. The springs 450 may be configured to have a variable rate. In one example, the springs 450 and/or the geometry of the associated link 430 may be arranged to have a constant force-displacement characteristic. Stated another way, a force acting in the extension direction may be constant or substantially constant regardless of the position of the top plate 414. In this example, no actuating force is required to operate the device. To the contrary, the device may be compressed, placed in the working position, and then released to apply a working force.

Optionally, the tensioner-balancer 410, specifically the top plate 414, may incorporate a tracking marker 486. The tracking marker 486 is operable such that, using an appropriate receiving device, the position and orientation of the top plate 414 (e.g., Z-height and/or tilt angle) may be determined by receipt and analysis at the receiving device of signals transmitted by the tracking marker 486.

The tensioner-balancer devices described above are suitable for various surgical procedures. In one procedure, the tensioner-balancer 40 is used to evaluate the knee and to model the articular surfaces of the knee over its range of motion. This modeling can include the generation of tool paths such as various bone cutting planes, tool paths, etc.

More particularly, the locus of points of contact of the femur F and the top plate 44 are modeled as a medial spline and a lateral spline.

To carry out this modeling, the tensioner-balancer is inserted between the femur F and the tibia T. In the example shown in FIG. 14, this is accomplished after having first made the tibial plateau cut. However, the tibial plateau cut is not required. For example, the tensioner-balancer 100 does require a tibial plateau cut.

The actuating instrument 70 is coupled to the tensioner-balancer 40. Femoral tracking marker 88 is implanted to the femur F. At least one of tibial tracking marker 90 and instrument tracking marker 86 are placed.

The tensioner-balancer 40 is extended to apply a load to the knee joint. While different modes of operation are possible, one exemplary mode is to extend the tensioner-balancer 40 until a predetermined distraction load (also referred to as distraction force) is applied. Feedback control or mechanical spring preload may then be used to maintain this distraction load, while the top plate 44 is permitted to pivot freely. One example of a suitable distraction load is approximately 130 N (30 lb.) to 220 N (50 lb.). As one option, the distraction load may be constant over the knee joint range of motion. As another option, the distraction may be a predetermined variable load, where the distraction load is correlated to knee joint position. As another option, the tensioner-balancer may be used to maintain a constant distraction gap while the knee joint is moved through its range of motion.

Figure 19:
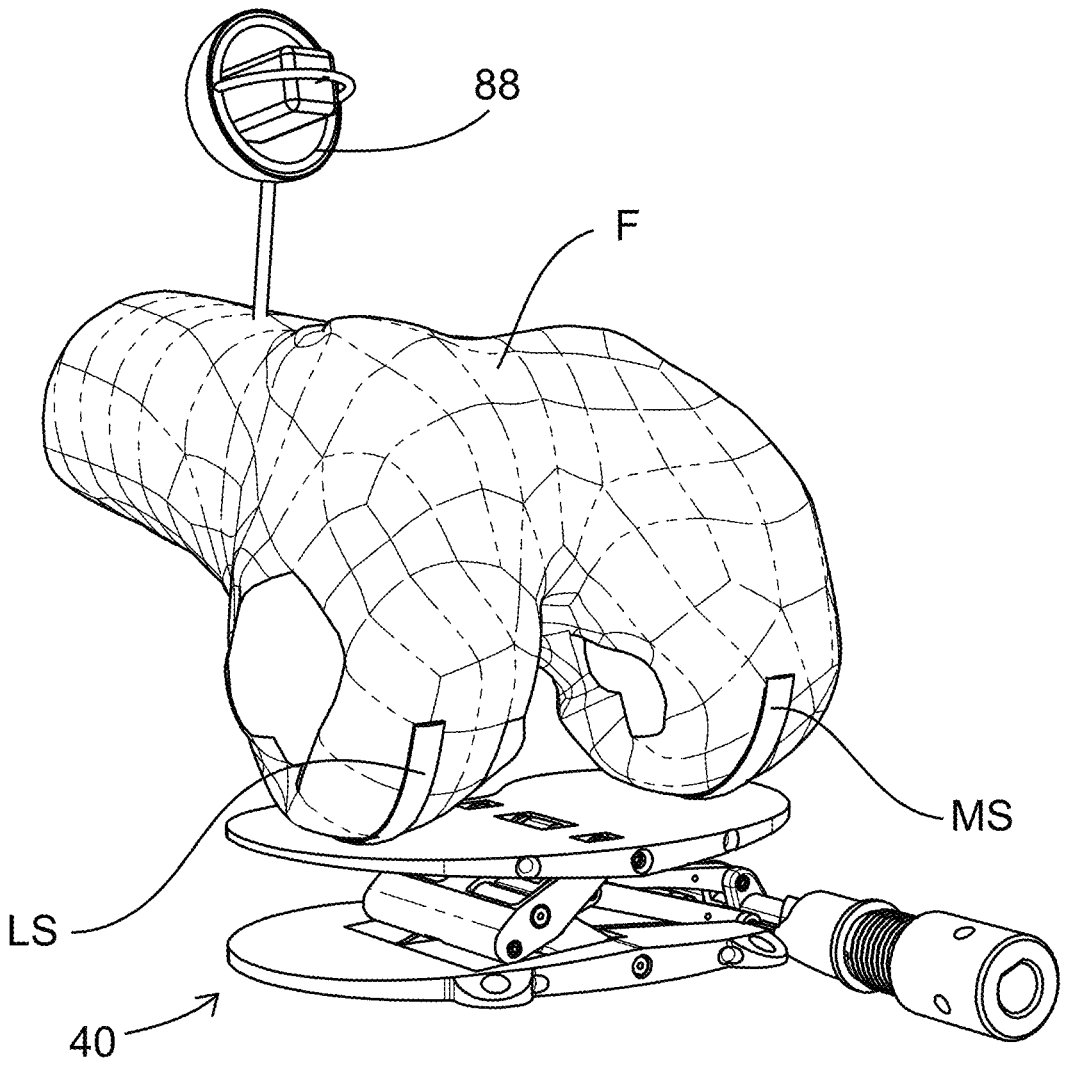
FIG. 19 is a perspective view showing a femur in contact with a tensioner-balancer.
Figure 20:
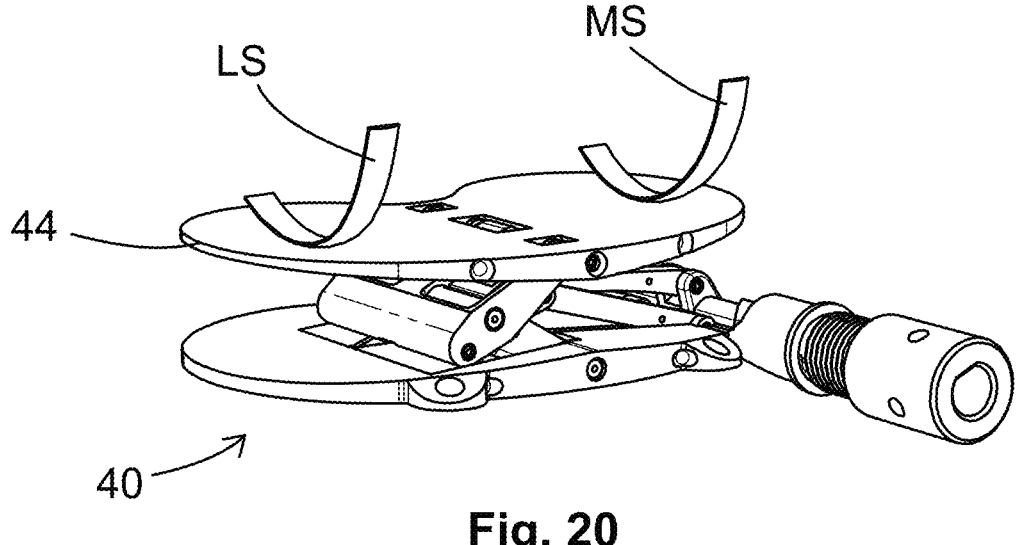
FIG. 20 is a perspective view showing plots of collected spline data superimposed on the top plate of a tensioner-balancer.
Figure 21:
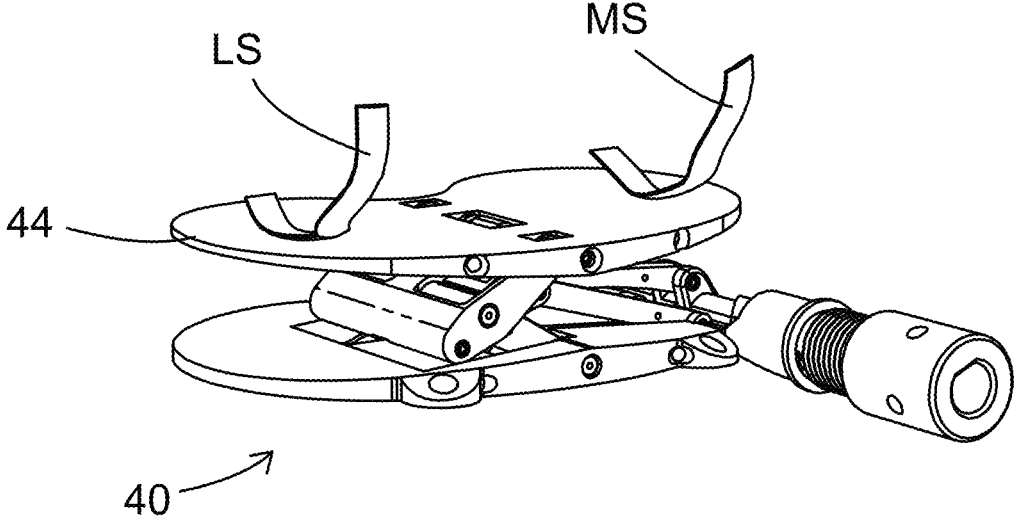
FIG. 21 is another perspective view showing plots of collected spline data superimposed on the top plate of a tensioner-balancer.
Figure 31:
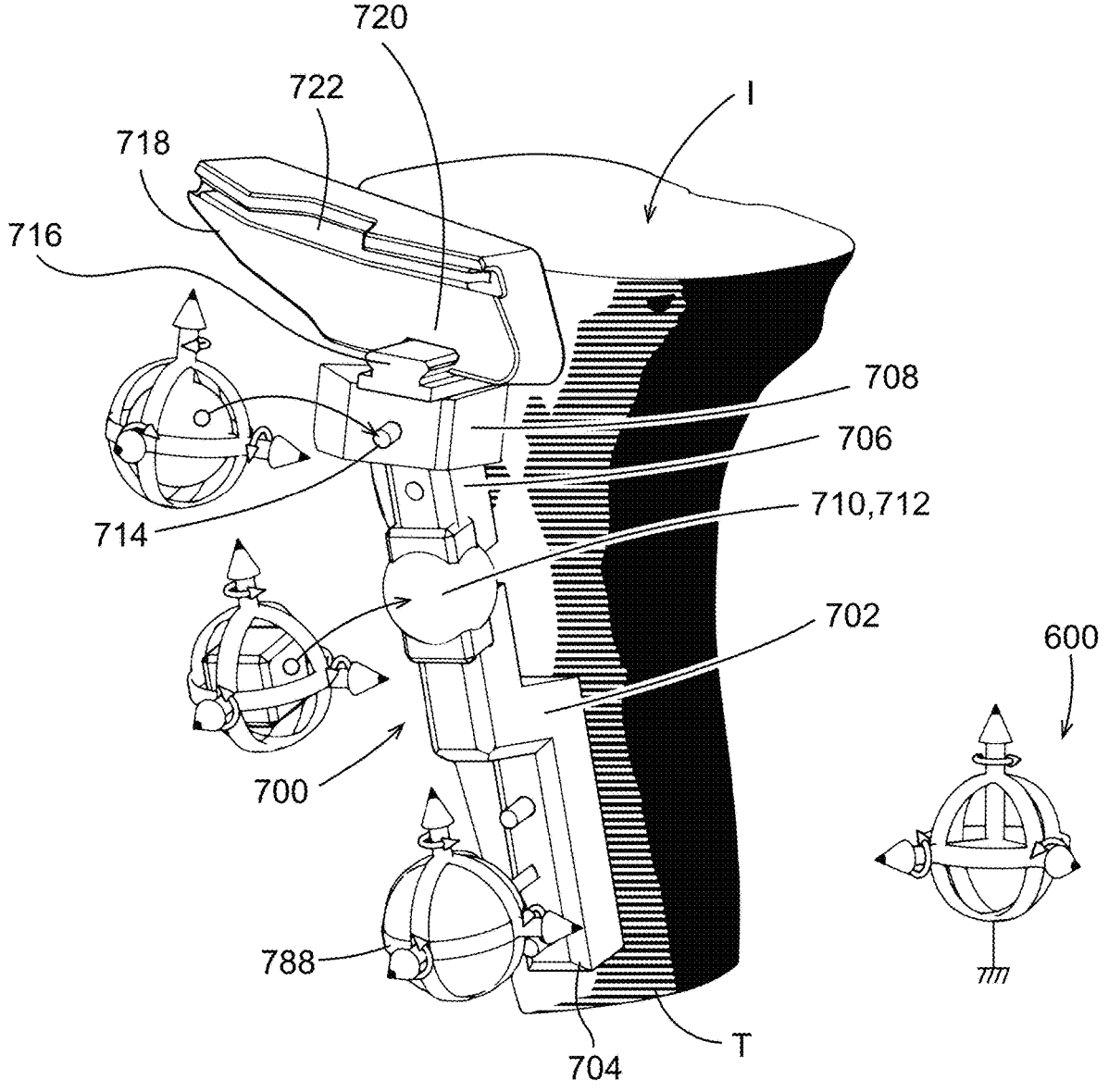
FIG. 31 is a perspective view of a portion of a human tibia having a jig positioning apparatus attached thereto.

The knee joint J is then moved through its range of motion from full extension to full flexion while collecting data from the tensioner-balancer 40 and tracking markers 86, 88, 90. Specifically, the instantaneous location of the load centers LC and MC are recorded and correlated to the flexion angle of the knee joint (as determined from the tracking marker data). The recorded data is represented by the medial spline "MS" and the lateral spline "LS" as shown in FIG. 19. FIGS. 20 and 31 show the splines superimposed on the top plate of the tensioner-balancer 40. FIG. 20 illustrates idealized or nominal shape splines. FIG. 21 illustrates splines indicative of discontinuities or "notching" which may be found in an actual or pathological knee joint J. The splines may be characterized by two or more points (a starting point and terminal point, with zero or more intermediary points in between), each with a location (defined by cartesian or polar coordinates relative to a fixed reference point defined by tracker on the tensioner-balancer baseplate), a direction, and a first and second derivative.

The spline information may be used to select an appropriate endoprosthesis, specifically a femoral component. Multiple femoral components of different sizes and articular surface profiles may be provided, and the one which has the best fit to the splines MS, LS may be selected for implantation. Alternatively, the spline information may be used to generate a profile for manufacture of a patient-specific femoral component.

Figure 22:
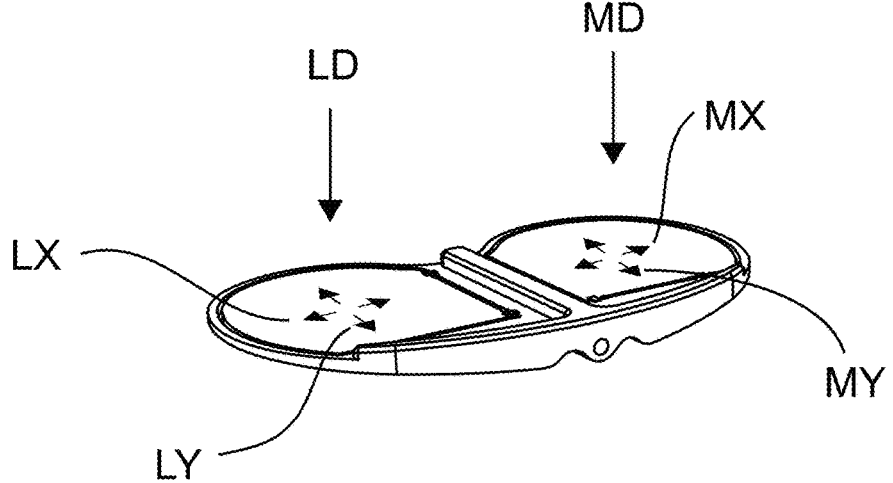
FIG. 22 is a diagram showing a tensioner-balancer labeled with data parameters.
Figure 22:
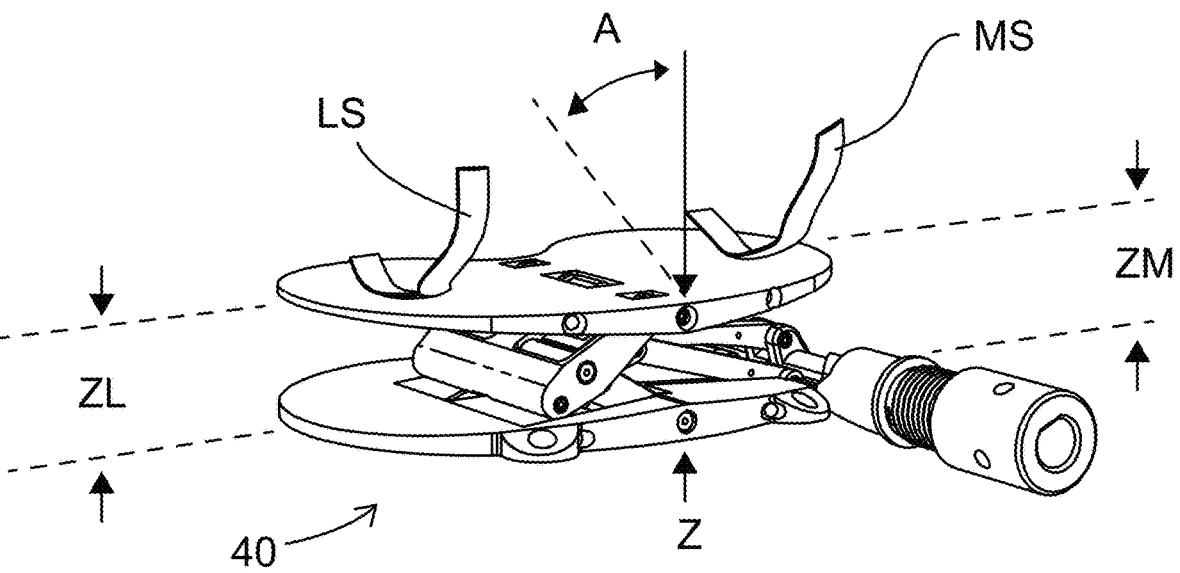
Figure 23:
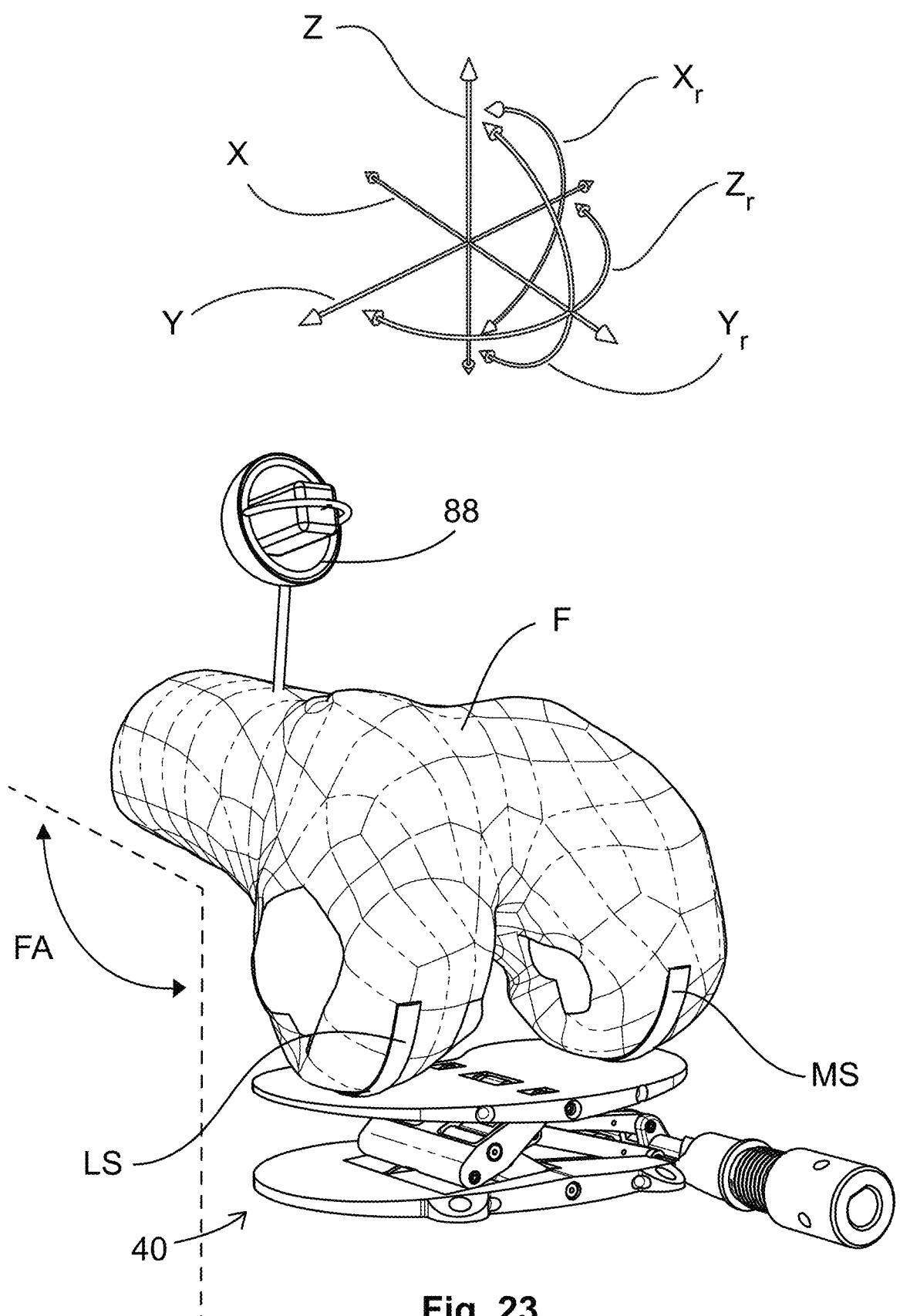
FIG. 23 is a diagram showing a knee joint and tensioner-balancer labeled with data parameters

With reference to FIGS. 22 and 23, it will be understood that the tensioner-balancer 40 and associated tracking apparatus may be used to collect the following data related to the knee joint: distraction height "Z" of the top plate 44, tilt angle "A" (i.e., varus-valgus) of the top plate 44), medial and lateral distraction heights "ZM", "ZL" (e.g., derived from the top plate distraction height and top plate tilt angle), the medial and lateral spline data, the position of the contact points of the femur F on the top plate (medial-lateral and anterior-posterior) (MX, MY, LX, LY), the distraction load on the medial and lateral condyles (MD, LD), the knee joint flexion angle "FA", and the abovementioned 6-DoF position data for each tracking marker (X, Y, Z position and Xr, Yr, Zr rotation).

In the case of the tensioner-balancer 100 shown in FIGS. 15 and 16, similar information can be collected, with a difference being that tilt angle data (varus-valgus) would be represented by differential "Z" heights between medial and lateral portions of the body 102 of the tensioner-balancer 100, as opposed to a direct tilt angle measurement.

In the case of the tensioner-balancer 410 shown in FIGS. 17 and 18, or similar simple mechanical device, similar information can be collected. In the case where the tensioner-balancer 410 is a lacking force sensor arrays on tibial interface surface, the spline data would be collected using conventional means, such as digitization of the medial and lateral condyles of the femur F using a physical stylus (not shown) or by use of other known non-contact digitization means such as optical scanning, LIDAR scanning, or time-of-flight scanning.

Figure 35:
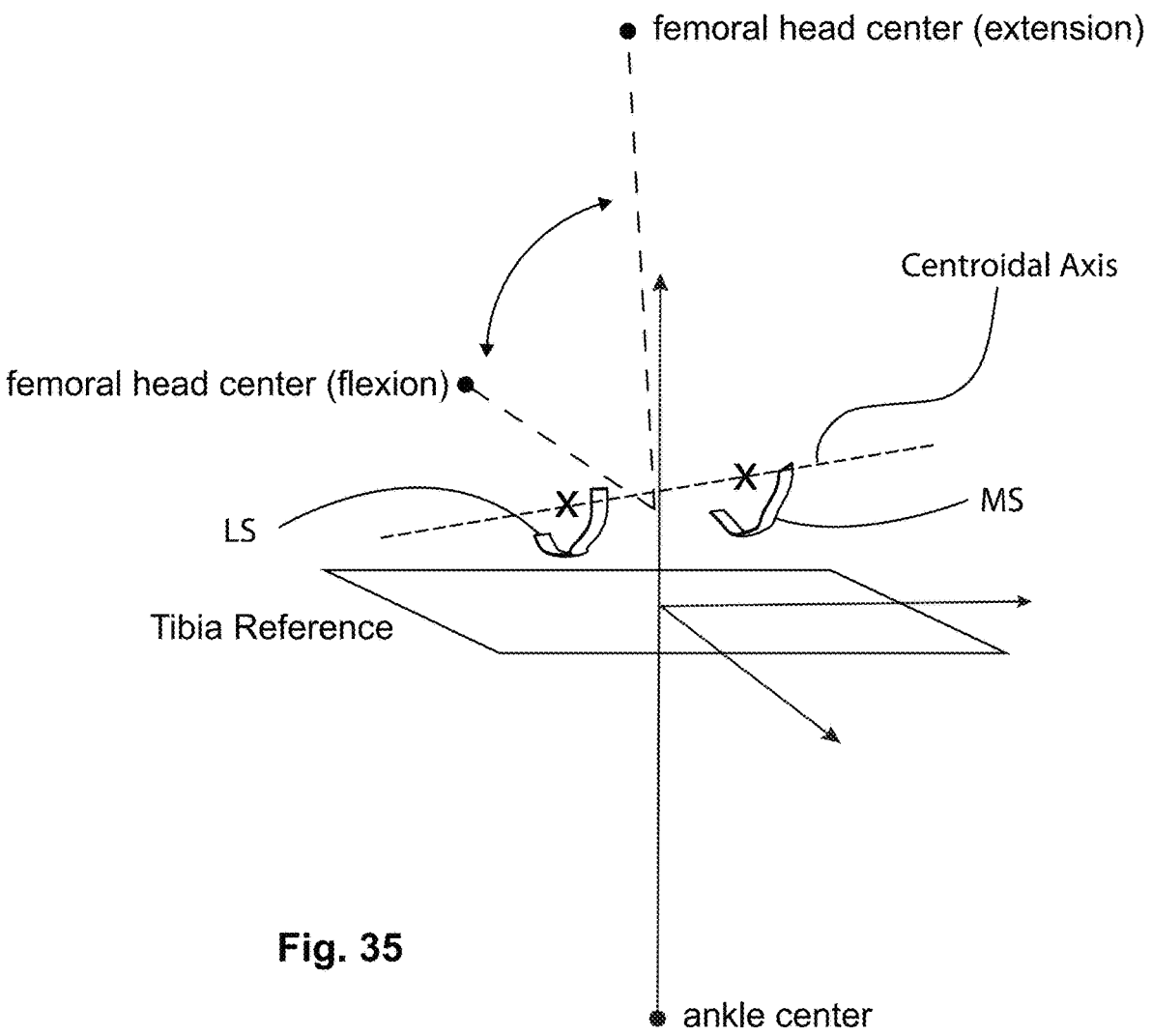
FIG. 35 is a diagram showing organization of data collected when modeling a knee joint.

FIG. 35 illustrates the organization of the collected data. It can be seen that the overall modeling of the complex 3D knee geometry can be reduced for practical purposes to a relatively small set of elements including: tibial plateau cut plane (or tibial reference plane), the medial and lateral splines, the position of the medial and lateral spine contacts on the tibial plateau cut plane, an axis or vector passing from the ankle center through the tibial plateau cut plane, a femoral axis passing through the femoral head, and a centroidal axis. The centroidal axis is a mathematical or digital construct generated by first determining an algorithmically best fit centroid of the lateral spline LS (marked with an "X" in FIG. 35) and determining an algorithmically best fit centroid of the medial spline MS (marked with an "X" in FIG. 35). The centroidal axis is a line passing through these two centroids.

The spline information may be used in conjunction with other information to determine appropriate cutting planes for the femur F. For example, the back surface 28 of the femoral component 14 has a known relationship to the articular surface 30. The desired final location and orientation of the articular surface 30 is known in relation to the top plate 44 of the tensioner-balancer 40, which serves as a proxy for the tibial component 12. The final location of the tibial component 12 is known in relationship to the position of the tibial tracking marker 90. Finally, the actual orientation and location of the femur F in relation to the other parts of the joint J is known from the information from the femoral tracking marker 88. Using appropriate computations, the orientation and location of the cutting planes of the femur F can be calculated and referenced to the position of the tensioner-balancer 40. A nominal distal femoral cutting plane 2 (FIG. 24) may be determined by anatomical analysis using known anatomical references and techniques. For example, this plane 2 could be uniformly spaced away from and parallel (when joint in extension) to the tibial cutting plane 1 (i.e., a nominal cut). Alternatively, this plane 2 could be at an oblique angle to the tibial cutting plane 1, in one or more planes (i.e., simple or compound tilted cut, potentially usable as a corrective cut).

Figure 24:
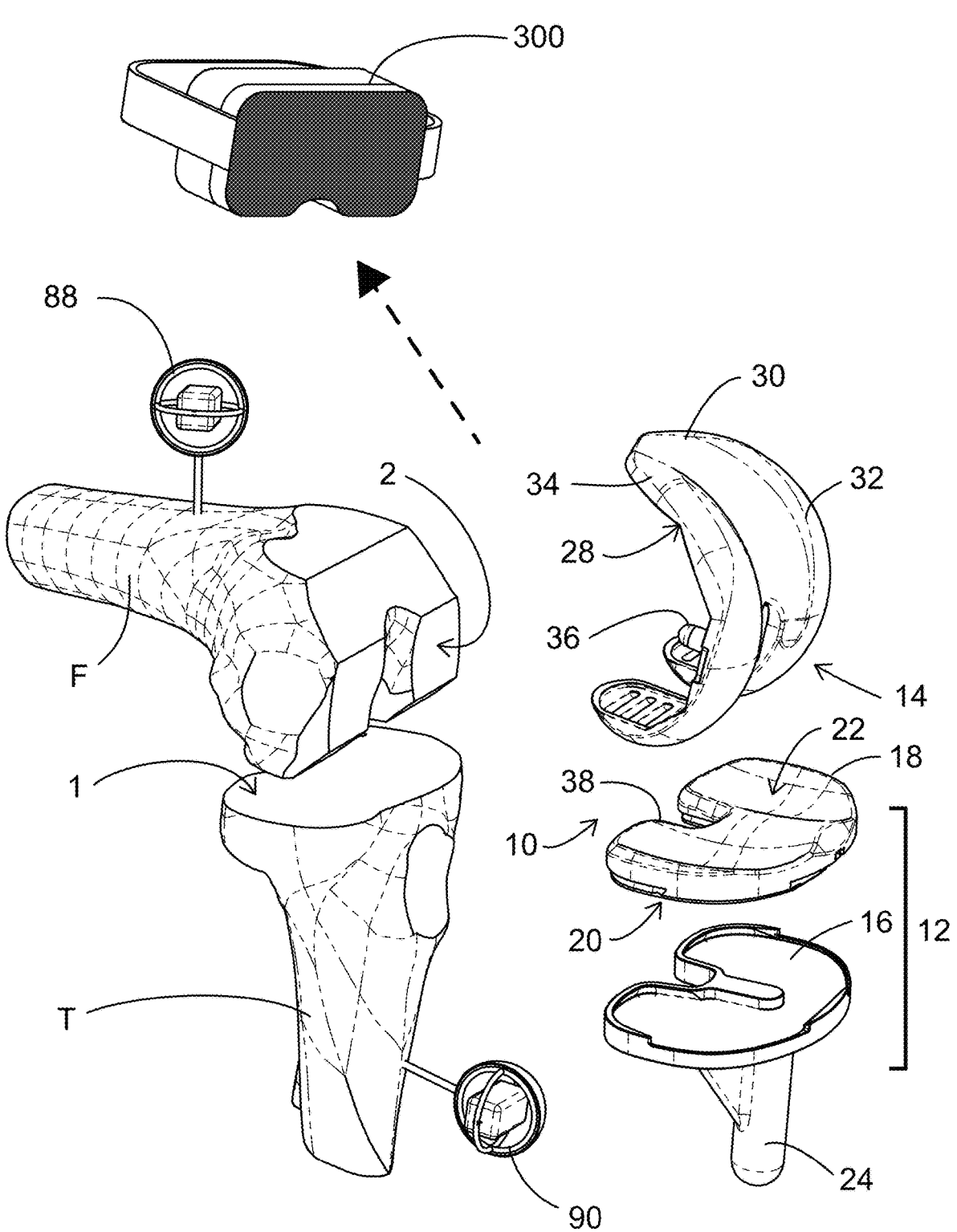
FIG. 24 is a perspective view of a human knee joint in conjunction with an exploded view of an endoprosthesis.
Figure 25:
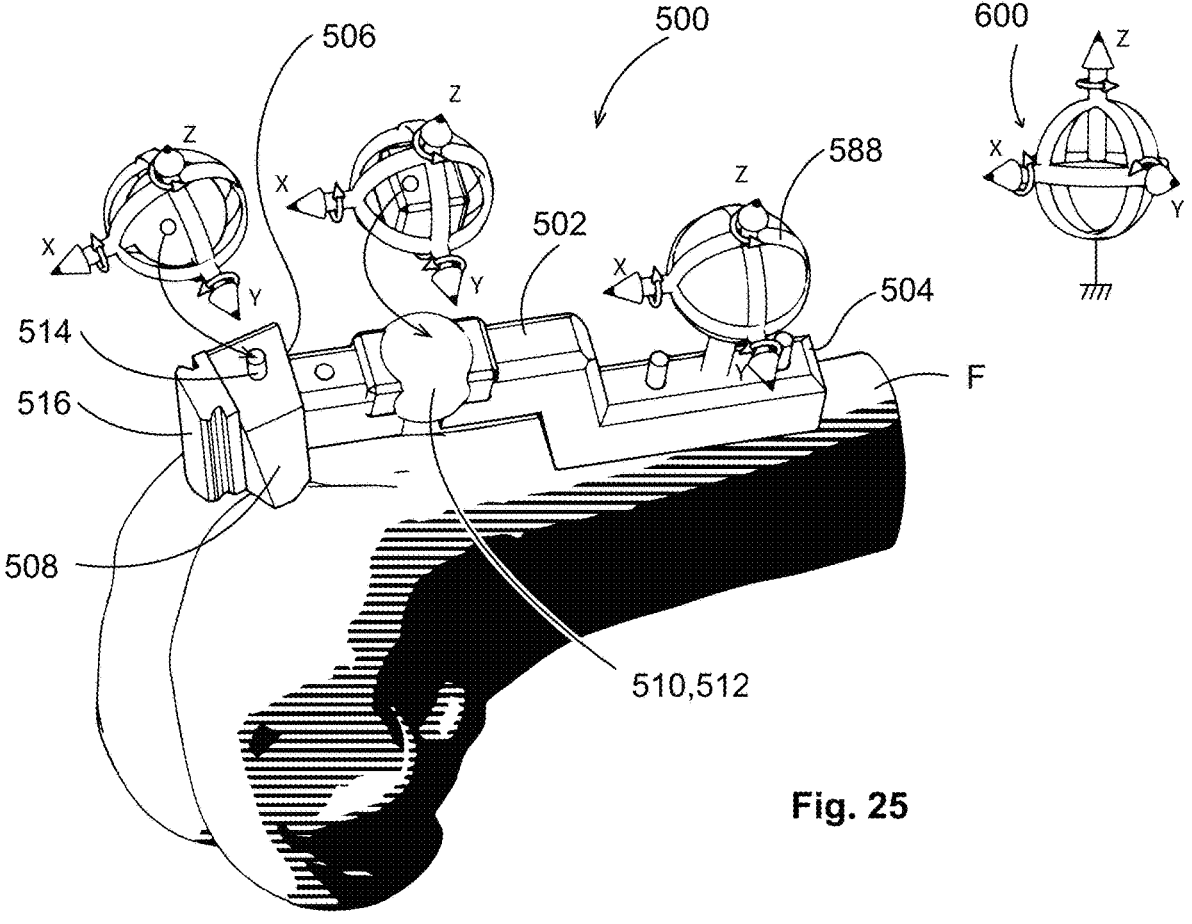
FIG. 25 is a perspective view of a portion of a human femur having a jig positioning apparatus attached thereto.

In the case where a tibial plateau cut 1 is not made before using the tensioner-balancer, similar computational techniques may be used to determine a nominal tibial cutting plane 1 (FIG. 24).

Once computed, the cutting plane information may be processed using appropriate coordinate transformations so that it can be expressed in relation to any one of the tracking markers 86, 88, or 90 which is present and available.

Information from the tensioner-balancer 40 and tracking markers may be used to make cuts, drill holes, or perform other surgical procedures using one or more jigs in conjunction with a jig positioning apparatus, seen in FIGS. 25-29.

The jig positioning apparatus 500 is shown as being attached to a human femur F. This may be accomplished with means such as bone screws or surgical pins (not shown). This is merely one example and it will be understood that the jig positioning apparatus 500 may be coupled to other bones of the knee joint J such as the tibia T, or any other bone.

The jig positioning apparatus 500 includes a mounting bracket 502 extending between a first end 504 and a second end 506. The mounting bracket 502 is substantially rigid, meaning that its material and sizing are such that it would not be expected to experience substantial deflections in ordinary surgical use.

The first end 504 is sized and shaped to conform closely to the bone in order to provide a secure attachment. In the illustrated example, the mounting bracket 502 is a shallow "Z" shape which offsets the second end 506 away from the bone.

The mounting bracket 502 may incorporate a tracking marker 588. The tracking marker 588 is operable such that, using an appropriate receiving device, the position and orientation of the receiving device relative to the tracking marker 588 may be determined by receipt and analysis at the receiving device of signals transmitted by the tracking marker 588. The function of the tracking marker 588 is to provide six degree of freedom (6-DOF) position information in a local coordinate reference space (i.e., position and orientation in each of three mutually perpendicular axes). Some devices or systems may be able to provide 6-DOF position information without requiring line of sight for signals (e.g., electromagnetic spectrum energy). For example, as illustrated, the tracking marker 588 may be configured as an inertial navigation device including one or more accelerometers and gyroscopic elements capable of providing angular rate information and acceleration data in 3D space.

The tracking marker 588, or any of the tracking markers described herein, may be optionally used in combination with an additional tracking marker or other similar device suitable for providing a common coordinate frame reference i.e., a common origin. In the illustrated example, a tracking marker 600 is shown as being disposed in a fixed position from which it can provide a coordinate reference. For example, the tracking marker 600 could be disposed in the room in which the surgical procedure is taking place. The position and orientation information of all of the other tracking marker described herein could be reported relative to the origin established by tracking marker 600.

It is noted that, where the jig mounting apparatus 500 is to be used, the tracking marker 588 mounted to the mounting bracket 502 would take the place of the independent tracking marker 88 implanted directly into the femur F as described above, in providing a positional reference for the femur F. In practice, the mounting bracket 502 with attached tracking marker 588 would be secured to the femur F prior to distracting the joint J and collecting the data as described above. The mounting bracket 502 may then remain in place throughout the remainder of the surgical procedure.

A mounting head 508 is coupled to the second end 506 of the mounting bracket 502. The mounting head 508 is coupled in such a way that it has six degrees of freedom of movement relative to the mounting bracket 502. For example, it may be able to translate three mutually perpendicular axes (e.g., X, Y, Z) and may be able to rotate about three mutually perpendicular axes (e.g., Xr, Yr, Zr).

To provide this freedom of movement for the mounting head 508, an adjustment mechanism 510 may be provided. The six degrees of freedom are indicated by the adjacent symbol. The adjustment mechanism 510 may be configured as a portion of the mounting bracket 502, or it may be portion of the mounting head 508, or it may be a separate element interconnecting the two components. The adjustment mechanism 510 may include means for manually driving the adjustment, such as knobs or levers. The adjustment mechanism 510 may include means for automatically driving the adjustment, such as motors or actuators. The adjustment mechanism 510 may include means for indicating the position of the adjustment, such as vernier scales. The adjustment mechanism 510 may include means for clamping or locking the adjustments in selected positions. The adjustment mechanism 510 may be configured to provide sufficient friction so as to stay in in a selected position once manually adjusted.

Figure 30:
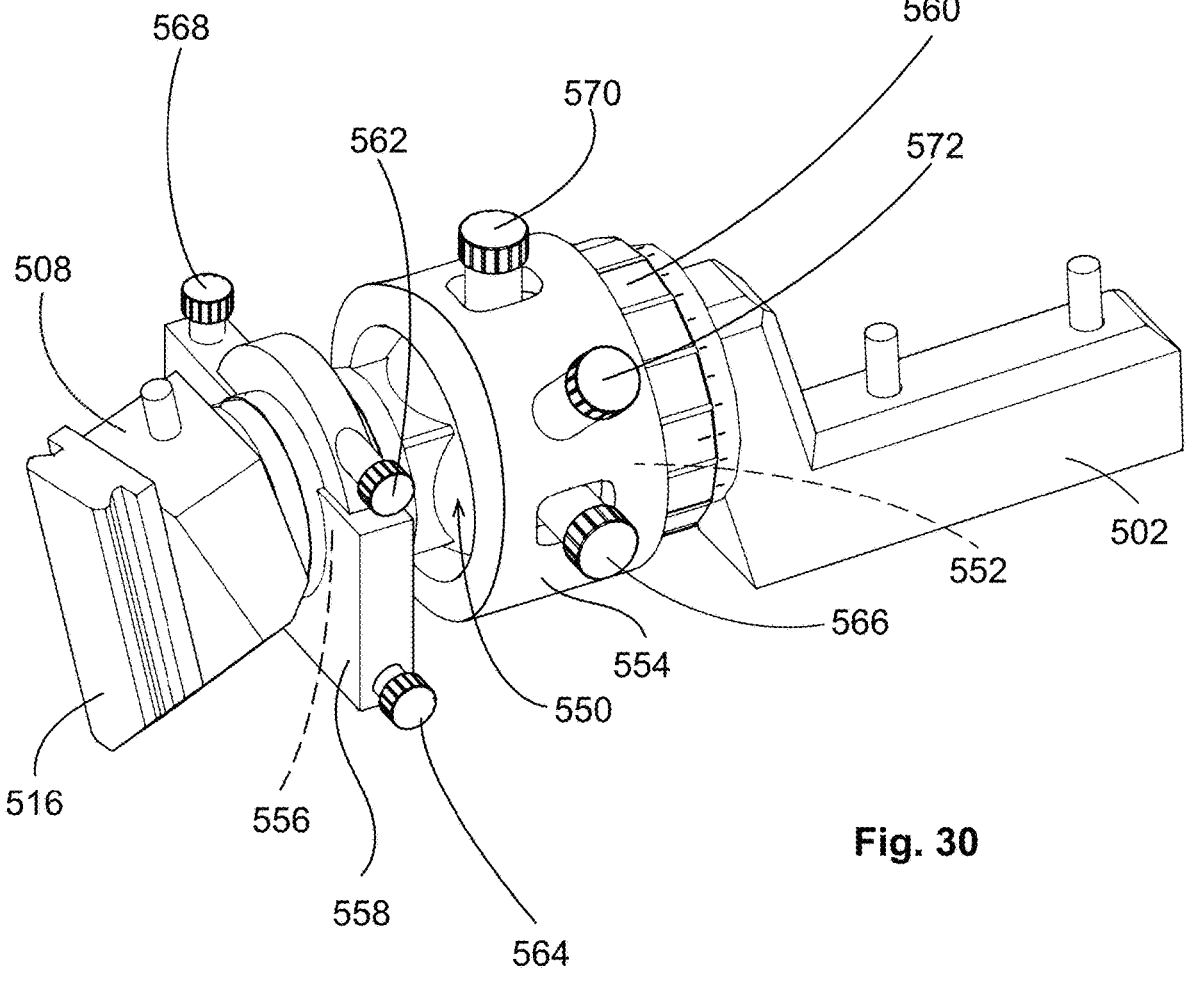
FIG. 30 is a perspective view of an example physical configuration of the jig positioning apparatus of FIG. 25.

FIG. 30 shows one possible physical configuration of the adjustment mechanism 510. This includes a ball element 550 having a first end 552 received in a socket element 554 and a second end 556 received in a bracket element 558. An adjusting ring 560 is mechanically coupled so as to drive the ball element 550 either forwards or backwards along an X axis. A X-rotation knob 562 mounted on the bracket element 558 is mechanically coupled so as to pivot the ball element 550 either clockwise or counterclockwise relative to the X axis.

A Y-knob 564 mounted on the bracket element 558 is mechanically coupled so as to drive the ball element 550 either forwards or backwards along the Y axis. A Y-rotation knob 570 mounted on the socket element 554 is mechanically coupled so as to pivot the ball element 550 either clockwise or counterclockwise relative to the Y axis.

A Z-knob 568 mounted on the bracket element 558 is mechanically coupled so as to drive the ball element 550 either forwards or backwards along the Z axis. A Z-rotation knob 566 mounted on the socket element 554 is mechanically coupled so as to pivot the ball element 550 either clockwise or counterclockwise about the Z axis.

Finally a locking knob 572 is mechanically coupled between the socket element 554 and the ball element 550 and arranged to move between an unlocked position which permits movement of the ball element 550 and a locked position which prevents movement of the ball element 550 (for example by application of a frictional load). Any of the knobs or adjacent components may be provided with indicia such as scales or Vernier scales, to indicate the positions of the associated adjustments.

Optionally, the adjustment mechanism 510 may include position feedback apparatus. In one example, the position feedback apparatus 512 may include some combination of linear and/or rotary encoders or resolvers or similar sensors operable to produce a signal representative of the relative position and orientation of the mounting head 508 to the mounting bracket 502. In one example, the position feedback apparatus may include a gyroscopic or accelerometer-based sensor.

The mounting head 508 may include a tracking marker 514. The tracking marker 514 is operable to provide precise orientation and position information of the mounting head 508 relative to the mounting bracket 502, as indicated by the adjacent symbol. In one example, the tracking marker 514 may be a miniaturized device working in an electromagnetic field to produce position and orientation information not requiring line of sight communication. Such devices are commercially available from Polhemus, Colchester, Vermont 05446 USA.

The mounting head 508 includes a mounting element, such as a rail, latch, or bracket. The illustrated example, the mounting element 516 is a dovetail-type rail. One example of a suitable mounting element is a rail conforming to the U.S. Department of Defense document MIL-STD-1913, commonly referred to as a "Picatinny" rail.

The jig positioning apparatus 500 may be used to attach and position various types of jigs to the bone.

Figure 26:
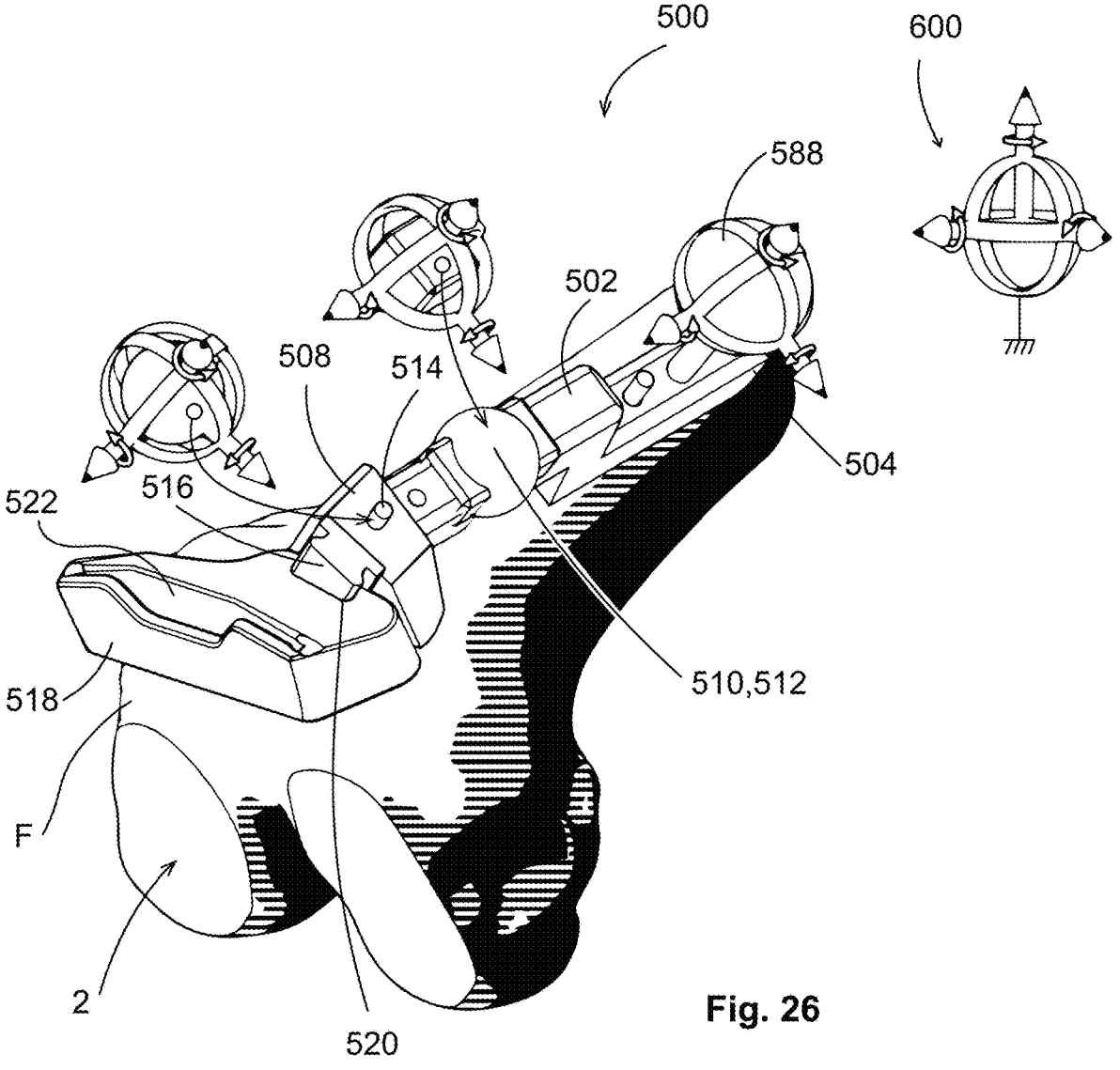
FIG. 26 is a perspective view of the jig positioning apparatus of FIG. 25, with a cutting block coupled thereto.

FIG. 26 shows an example in which a cutting block 518 is coupled to the mounting head 508. The cutting block 518 includes a mounting element 520 which is complementary to the mounting element 516 of the mounting head 508. This mounting element 520 could be, for example, a rail, latch, or bracket. In the illustrated example, the mounting element 520 is a dovetail-type groove complementary to the dovetail-type rail. The cutting block 518 may incorporate a clamp, stop, latch, or other structure operable in conjunction with the mounting element 520 to secure it in a fixed position relative to the mounting head 508.

The cutting block 518 includes a guide surface 522 which is a planar surface or slot configured to guide a flat blade (not shown) of a surgical cutting instrument, such as a conventional oscillating bone saw, a wire saw, or other contact or non-contact device for producing the femoral resections. In the illustrated example, the guide surface 522 is configured to provide a reference for making a distal femoral cut 2. The guide surface 522 is an example of a "reference feature".

Figure 27:
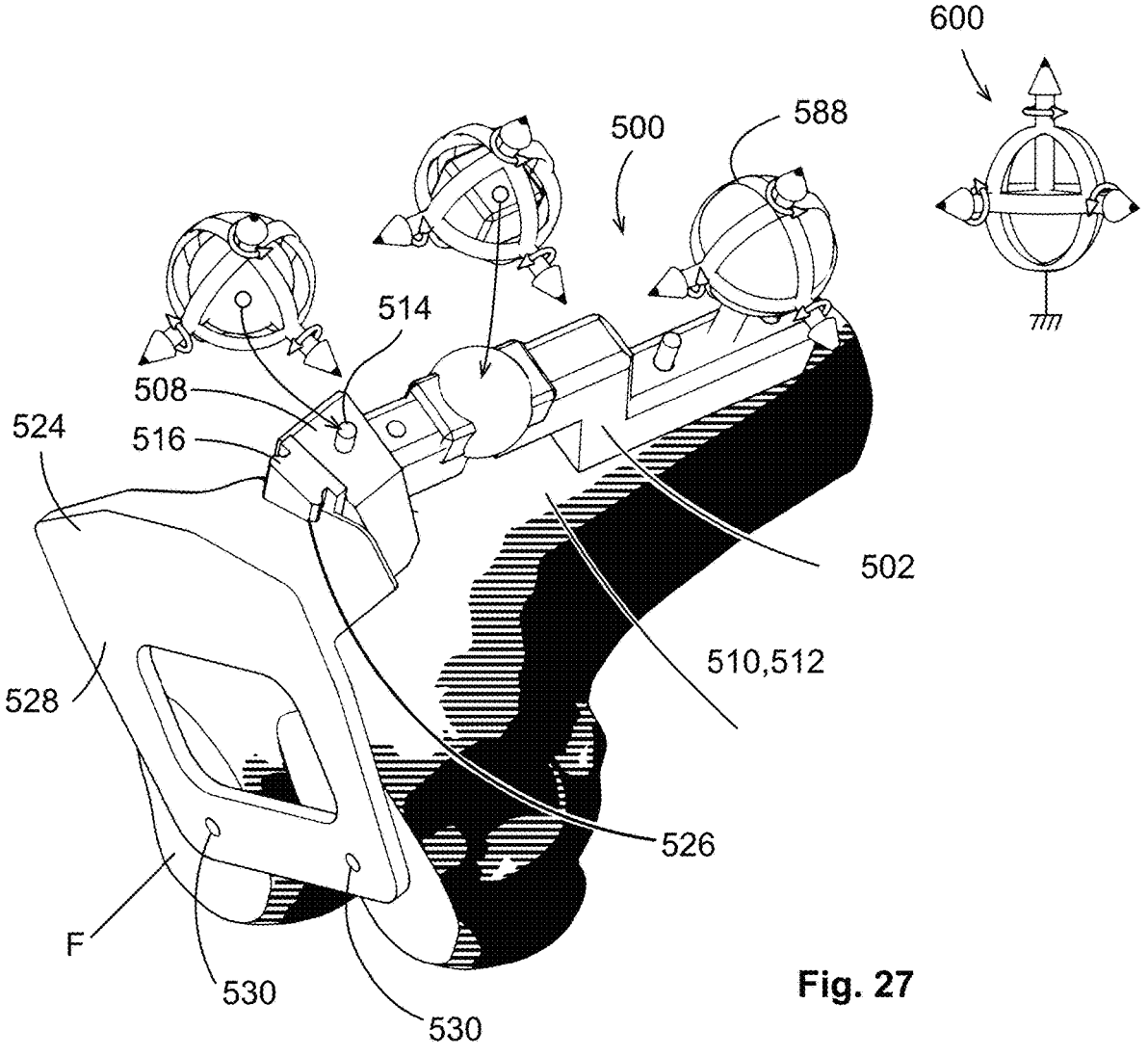
FIG. 27 is a perspective view of the jig positioning apparatus of FIG. 25, with a drilling guide coupled thereto.

FIG. 27 shows an example in which a drilling guide 524 is coupled to the mounting head 508. The drilling guide 524 includes a mounting element 526 which is complementary to the mounting element 516 of the mounting head 508. This mounting element 526 could be, for example, a rail, latch, or bracket. In the illustrated example, the mounting element 526 is a dovetail-type groove complementary to the dovetail-type rail. The drilling guide 524 may incorporate a clamp, stop, latch, or other structure operable in conjunction with the mounting element 526 to secure it in a fixed position relative to the mounting head 508.

The drilling guide 524 includes a plate 528 which extends over the distal cut surface of the femur F. The plate includes one or more guide holes 530 sized to receive an appropriate drill bit (not shown). The guide holes 530 are an example of "reference feature".

Figure 28:
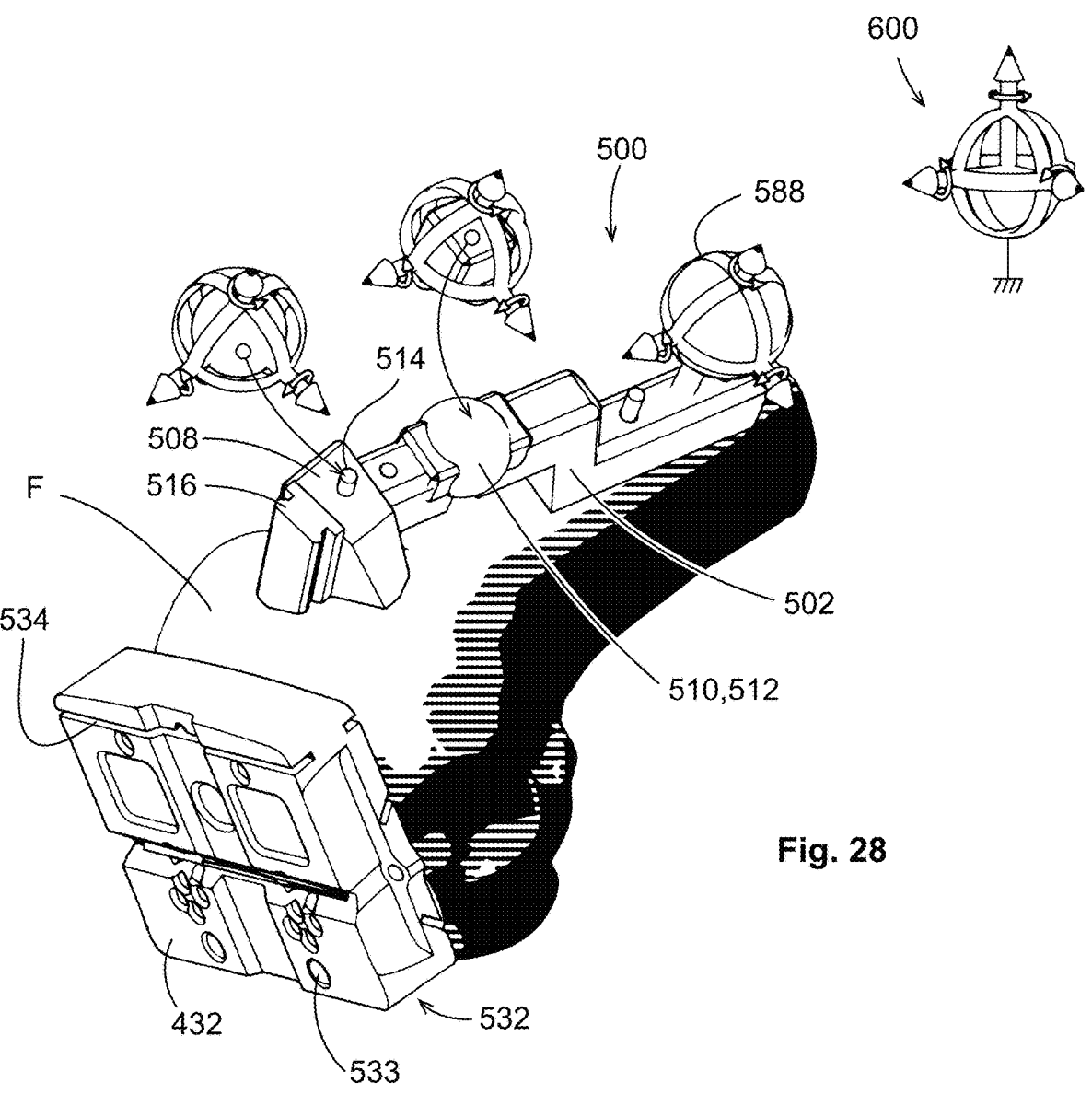
FIG. 28 is a perspective view of the jig positioning apparatus of FIG. 25, with a 4-in-1 block coupled thereto.
Figure 29:
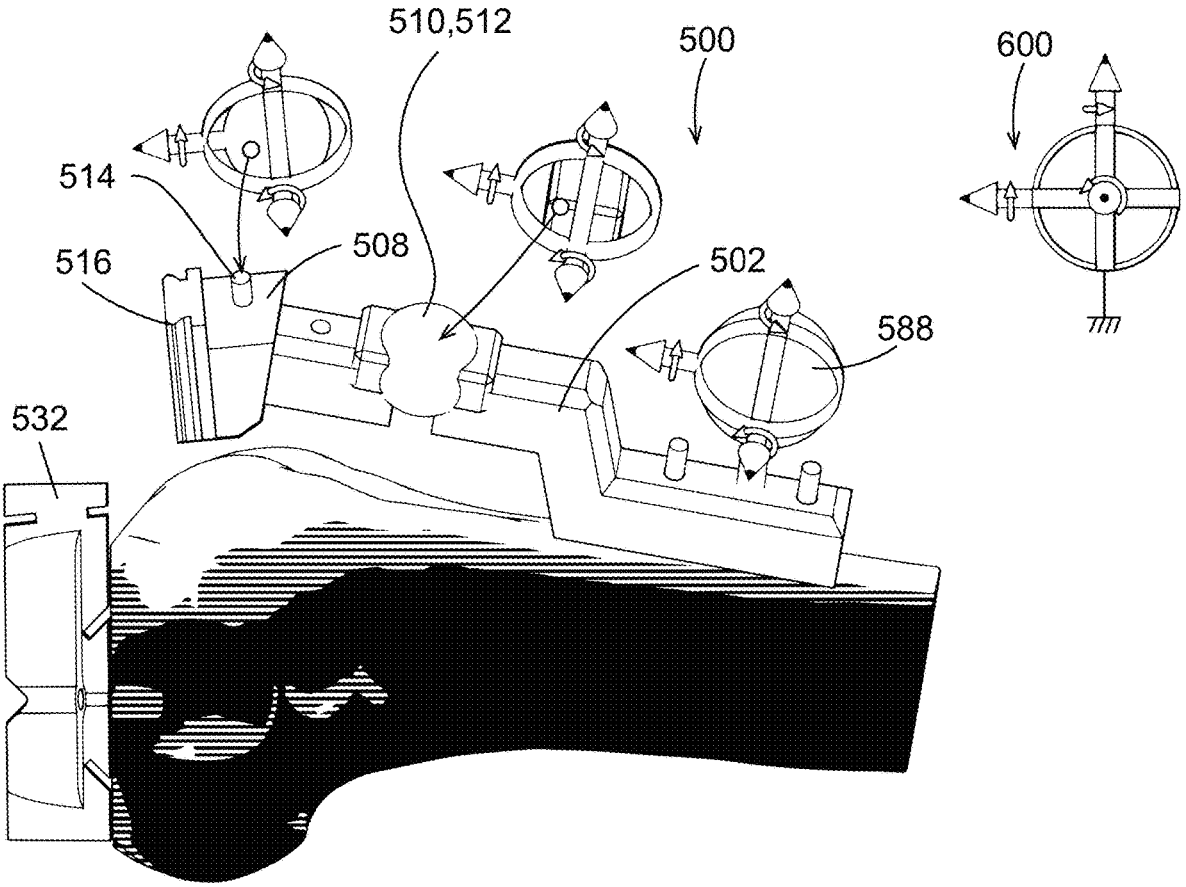
FIG. 29 is a side view of the jig positioning apparatus and 4-in-1 block of FIG. 28.

FIGS. 28 and 29 show an example in which a 4-in-1 block 532 is coupled to the distal cut surface of the femur F. The 4-in-1 block 532 includes mounting holes 533 which are aligned with the pattern of holes formed by use of the drilling guide 524. The 4-in-1 block 532 may be secured to the bone using bone screws or surgical pins (not shown) passing through these holes and into the femur F.

The 4-in-1 block 532 includes one or more guide surfaces 534 which our planar surface configured to guide a flat blade (not shown) of a surgical cutting instrument, such as a conventional oscillating bone saw. In the illustrated example, the guide surfaces 534 are configured to provide a reference for making a posterior femoral cut, anterior cuts, and/or chamfer cuts. The guide surfaces 534 are examples of "reference features".

Information from the tracking marker 514 of the mounting head 508, or from the position feedback apparatus of the adjustment mechanism 510 may be used to precisely determine the position in 3D space of the mounting head 508. Once the cutting planes are determined using the process described above, appropriate coordinate transformations may be used to determine the position of the mounting head 508 required to bring the guide surface 522 (FIG. 26) of the cutting block 518 (or reference feature of one of the other describes jigs) into position to make the correct cut (e.g., distal femoral cut 1). Stated another way, the tracking marker information may be used to determine the real-time position of the reference feature of the attached jig.

Figure 33:
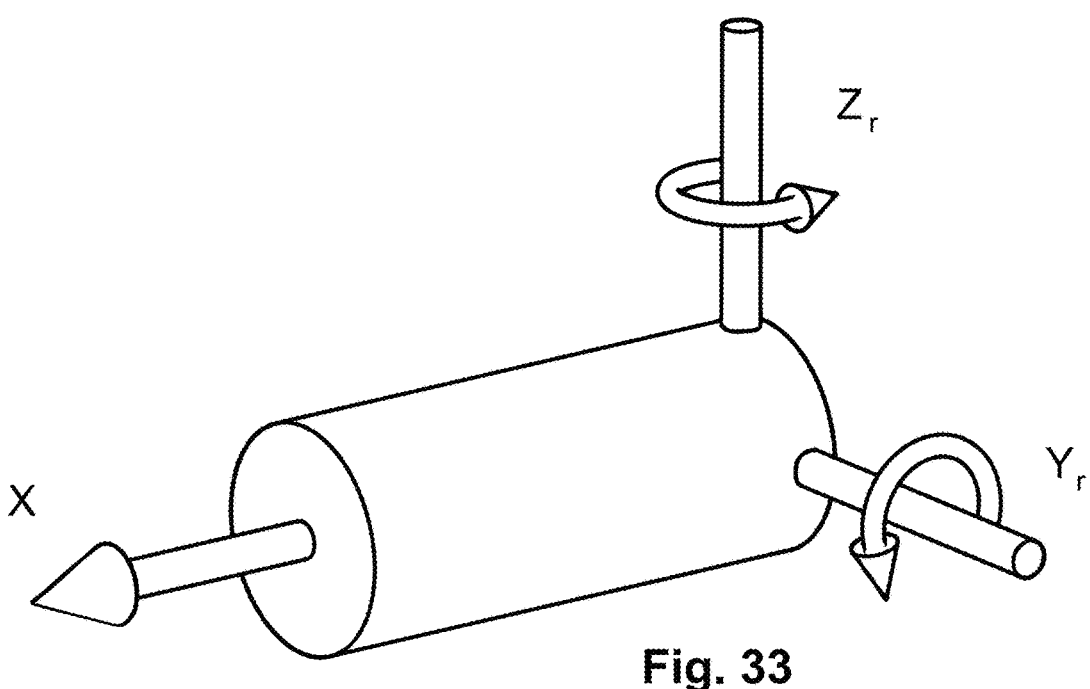
FIG. 33 is a diagram showing a set of adjustments for a surgical jig.

Referring to FIG. 33, it will be understood the cutting block 518 can be brought into alignment with the distal femoral cutting plane 2 by rotation about two mutually perpendicular axes (Y, Z) and translation about the third axis (X). This is three degrees of freedom of movement out of a possible six degrees of freedom.

The computed position of the mounting head 508 may be relayed to the surgeon in the form of appropriate visual or graphical feedback or guidance. The guidance may be provided in the form of information displayed on the remote display 84 described above. For this purpose, 2-way data communications may be provided between and among the head 508, the tracking markers 86, 88, or 90, and the remote display 84. Alternatively, the cutting guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 300, FIG. 24).

The visual or graphical guidance may be formatted as text or numerical data or as graphics. In one example, the surgeon may be provided sequential instructions and feedback to make adjustments. For example, if an X-axis adjustment is to be increased, the guidance could be in the form of red graphics when the adjustment is far from the desired position, changing to yellow graphics as the surgeon increases the X-axis value approaching the desired position, and finally changing to green graphics when the adjustment falls within a range of allowable positions.

It will be understood that the apparatus described above provides multiple options for specific procedures to determine the bone cutting planes. The physical adjustment may be manual or automated, and the determination of the correct position may be an open-loop process or a closed-loop process. Nonlimiting examples of possible procedures are set forth below.

In one procedure, a surgeon may manually adjust the adjustment mechanism 510 and/or mounting head 508, referencing feedback from the tracking marker 514 of the mounting head 508.

In one procedure, a surgeon may manually adjust the adjustment mechanism 510 and/or mounting head 508, referencing feedback from the position feedback apparatus 512.

In one procedure, a surgeon may manually adjust the adjustment mechanism and/or mounting head 508, referencing markings on the position adjustment mechanism 510 such as vernier scales.

In one procedure, the adjustment mechanism 510 may automatically drive the mounting head 508 to required position referencing feedback from the tracking marker of the mounting head.

After the femoral distal cut is made, the cutting block 518 may be removed and the drilling guide 524 may be installed. A drill may be used to "spot drill" or drill small locating holes for locating the 4-in-1 block.

Figure 34:
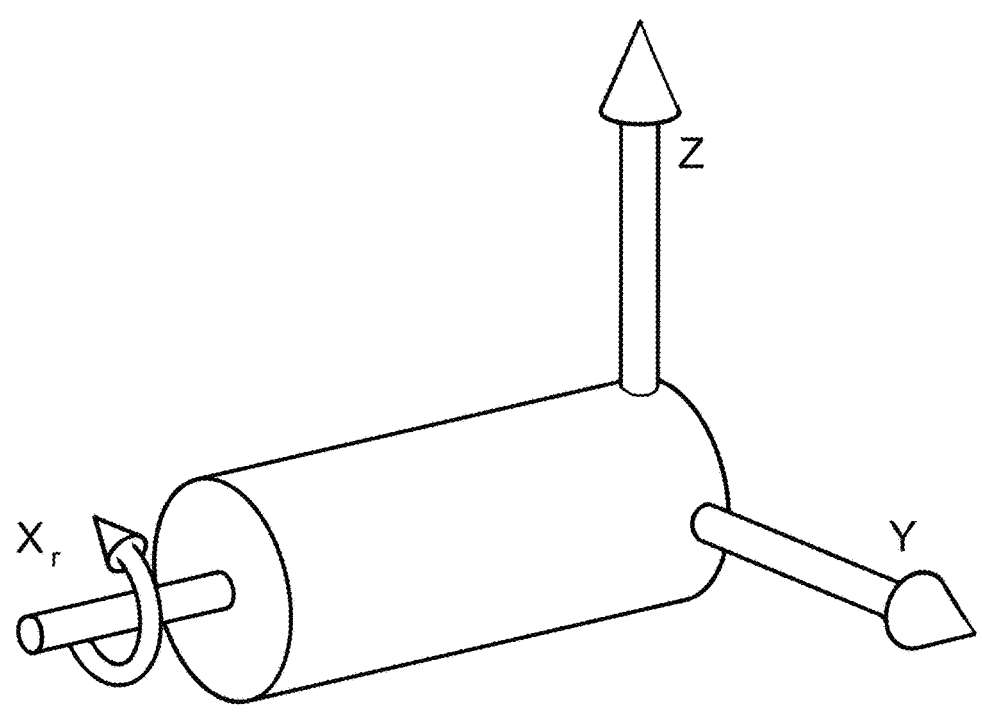
FIG. 34 is a diagram showing a set of adjustments for a surgical jig.

Referring to FIG. 34, it will be understood the drilling guide 524 can be brought into alignment with the femur F by translation about two mutually perpendicular axes (Y, Z) and rotation about the third axis (X). This is three degrees of freedom of movement out of a possible six degrees of freedom.

While it is possible to align the drilling guide 524 in a separate process, it will be understood that with appropriate selection of the dimensions of the drilling guide 524, and if the mounting head 508 is brought into an appropriate position and orientation in all six degrees of freedom in the initial alignment step described above, then no further adjustment to the position of the mounting head 508 is required. Stated another way, the mounting at 508 may be aligned one time. Then the cutting block 518 may be attached and the distal femoral cut made. Then the cutting block 518 may be simply removed and the drilling guide 524 attached.

Once locating holes have been spot drilled, the drilling guide 524 may be removed and the 4-in-1 block 532 may be secured to the femur F. Additional cuts such as the anterior cut, posterior cut, and chamfer cuts may be made using the 4-in-1 block 532 as a tooling guide.

A jig positioning apparatus 700 suitable for use with the tibia T is shown in FIG. 31. The overall construction of the apparatus 700 is similar to that of apparatus 500 described above. Elements of the apparatus 700 not explicitly describe may be taken to be identical to the corresponding components of apparatus 500. The jig positioning apparatus 700 includes a mounting bracket 702 extending between a first end 704 and a second end 706. The mounting bracket 702 may incorporate a tracking marker 788 similar to tracking marker 588.

A mounting head 708 is coupled to the second end 706 of the mounting bracket 702. The mounting head 708 is coupled in such a way that it has six degrees of freedom of movement relative to the mounting bracket 702. (It is noted that minimally, to perform a tibial plateau cut, the mounting at 708 only needs 3 degrees of freedom, namely to rotary and one axial, as described above for the distal femoral cut). To provide this freedom of movement for the mounting head 708, an adjustment mechanism 710 may be provided. The adjustment mechanism 710 may be configured as a portion of the mounting bracket 702, or it may be portion of the mounting head 708, or it may be a separate element interconnecting the two components.

Optionally, the adjustment mechanism 710 may include position feedback apparatus. In one example, the position feedback apparatus 712 may include some combination of linear and/or rotary encoders or resolvers or similar sensors operable to produce a signal representative of the relative position and orientation of the mounting head 708 to the mounting bracket 702. In one example, the position feedback apparatus may include a gyroscopic or accelerometer-based sensor.

The mounting head 708 may include a tracking marker 714. The tracking marker 714 is operable to provide precise orientation and position information of the mounting head 708 relative to the mounting bracket 702. In one example, the tracking marker 714 may be a miniaturized device working in an electromagnetic field to produce position and orientation information not requiring line of sight communication. Such devices are commercially available from Polhemus, Colchester, Vermont 05446 USA.

The mounting head 708 includes a mounting element, such as a rail, latch, or bracket. The illustrated example, the mounting element 716 is a dovetail-type rail. One example of a suitable mounting element is a rail conforming to the U.S. Department of Defense document MIL-STD-1913, commonly referred to as a "Picatinny" rail.

The jig positioning apparatus 700 may be used to attach and position various types of jigs to the bone.

FIG. 31 shows an example in which a cutting block 718 is coupled to the mounting head 708. The cutting block 718 includes a mounting element 720 which is complementary to the mounting element 716 of the mounting head 708. This mounting element 720 could be, for example, a rail, latch, or bracket. In the illustrated example, the mounting element 720 is a dovetail-type groove complementary to the dovetail-type rail. The cutting block 718 may incorporate a clamp, stop, latch, or other structure operable in conjunction with the mounting element 720 to secure it in a fixed position relative to the mounting head 708.

The cutting block 718 includes a guide surface 722 which is a planar surface or slot configured to guide a flat blade (not shown) of a surgical cutting instrument, such as a conventional oscillating bone saw. In the illustrated example, the guide surface 722 is configured to provide a reference for making a tibial plateau cut 1.

Figure 32:
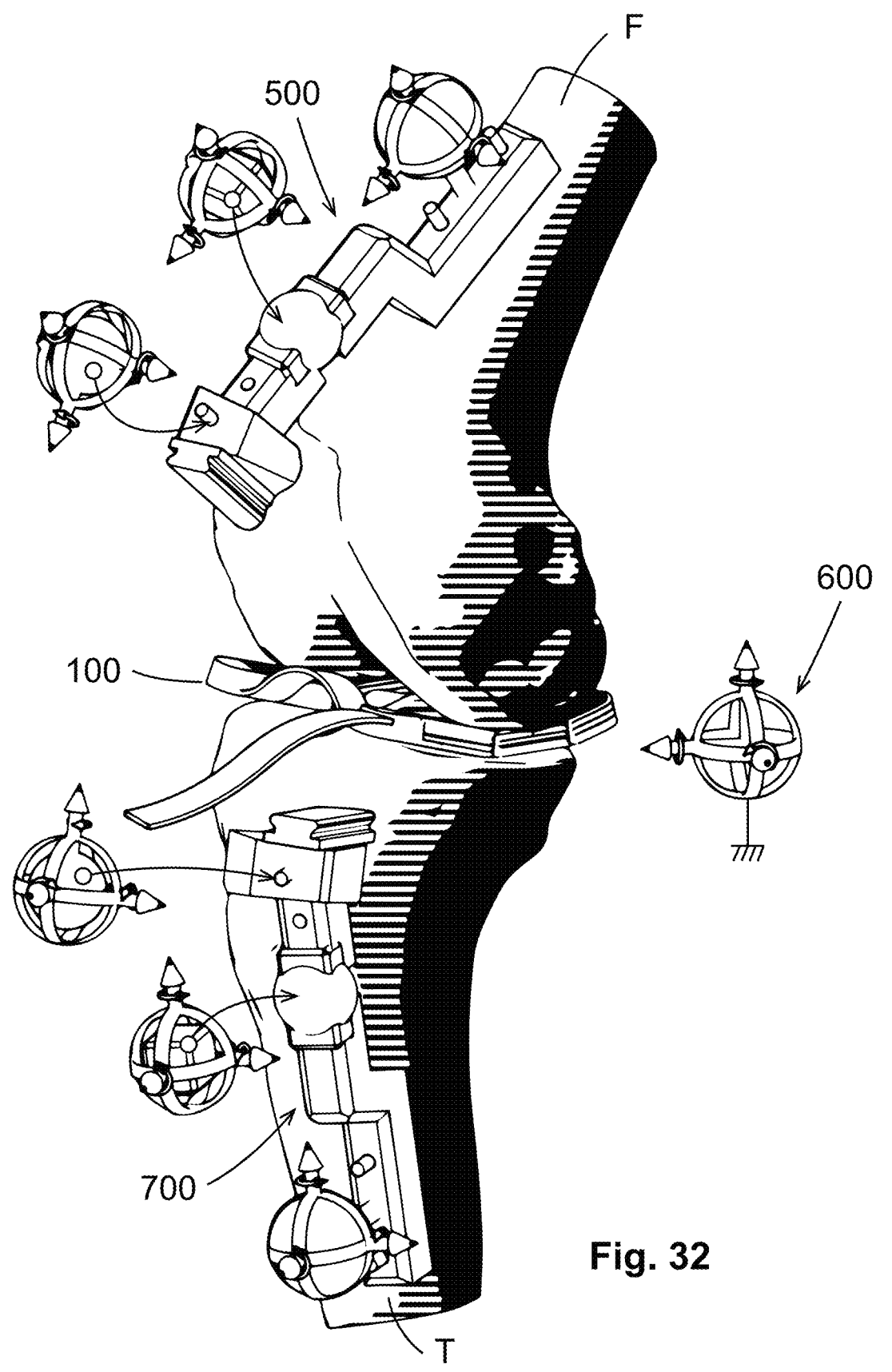
FIG. 32 is a perspective view of a human knee joint having jig positioning apparatus attached thereto.

FIG. 32 shows a knee joint J with the jig positioning apparatus 500 affixed to the femur F and the jig positioning apparatus 700 affixed to the tibia T. A tensioner-balancer 100 of the type shown in FIGS. 15 and 16 is inserted between the articular surfaces of the femur F and tibia T. In this configuration, no tibial plateau cut has yet been made.

Thus configured, the knee joint J may be distracted with the tensioner-balancer 100. Load may be measured with tensioner-balancer 100 while position information is collected using the tracking markers 588, 788. Once joint modeling is complete and cutting planes are determined as described elsewhere herein, cuts may be made on the femur F using the jig positioning apparatus 500, and cuts may be made on the tibia T using the jig positioning apparatus 700. Because each jig positioning apparatus provides independent position reference relative to the bone to which it is affixed, the cuts may be made in any order. For example, in contrast to conventional knee arthroplasty techniques, the tibial plateau cut T could be made after cuts are made on the femur F.

Figure 36:
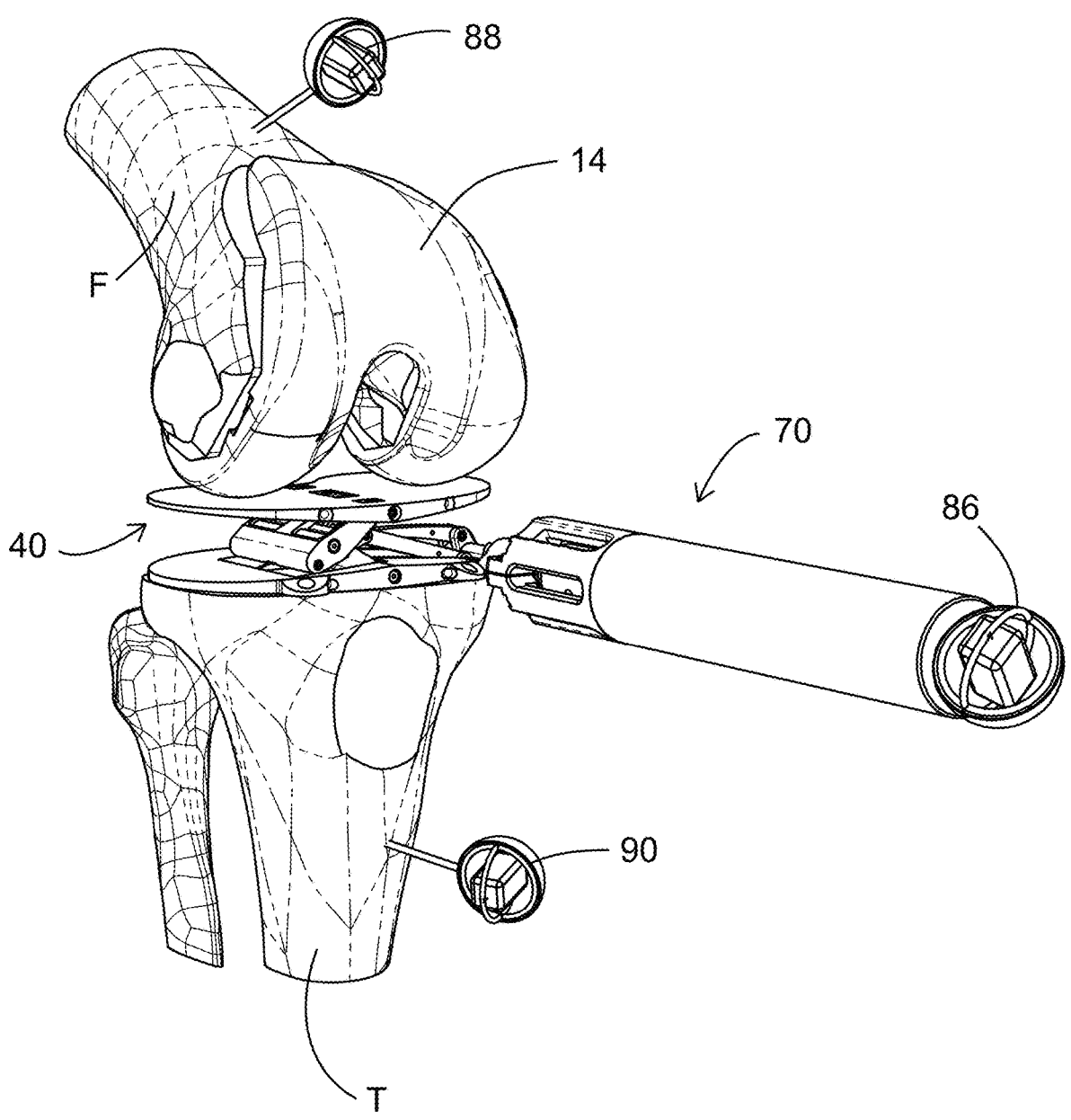
FIG. 36 is a perspective view of a human knee joint having a trial endoprosthetic device implanted, in conjunction with a tensioner-balancer.

As seen in FIG. 36, the tensioner-balancer 40 may be used with a trial implant (femoral component 14) to collect data and evaluate the femoral component 14.

The apparatus and method described herein will permit knee arthroplasty with improved patient outcomes with a minimum amount of added equipment and procedures.

The apparatus and techniques described herein are also applicable to surgical procedures and arthroplasty on other joints. The apparatus can be used to distract, track, and proceed with corrective actions based on distraction feedback. For example, these techniques may be used on hip or shoulder joints.

The foregoing has described apparatus and methods for joint arthroplasty. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. An apparatus for securing and positioning a jig on a human joint, comprising:
   a mounting bracket;
   a first tracking marker coupled to the mounting bracket, configured to generate a first signal representative of the position and orientation in space of the mounting bracket;
   a mounting head coupled to a distal end of the mounting bracket by an adjustment mechanism configured to permit six degree of freedom of movement of the mounting head relative to the mounting bracket;
   position feedback means configured to generate a second signal representative of the position and orientation of the mounting head relative to the mounting bracket, wherein the position feedback means comprises a second tracking marker disposed in the adjustment mechanism;
   a mounting element coupled to the mounting head;
   an electronic receiving device configured to receive the first and second signals; and
   a display configured to display the position and orientation of the mounting head relative to the mounting bracket.

2. The apparatus of claim 1, wherein the display is a virtual reality headset.

3. The apparatus of claim 1, wherein the display is an augmented reality headset.

4. The apparatus of claim 1, wherein the display is configured to present instructions for manipulating the adjustment mechanism.

5. The apparatus of claim 1, wherein the display is configured to present an indication whether the adjustment mechanism is in a desired position or not.

6. An apparatus for securing and positioning a jig on a human joint, comprising:
   a mounting bracket;
   a first tracking marker coupled to the mounting bracket, configured to generate a first signal representative of the position and orientation in space of the mounting bracket;
   a mounting head coupled to a distal end of the mounting bracket by an adjustment mechanism configured to permit six degree of freedom of movement of the mounting head relative to the mounting bracket;
   position feedback means configured to generate a second signal representative of the position and orientation of the mounting head relative to the mounting bracket, wherein the position feedback means comprises:
      at least one position transducer disposed in the adjustment mechanism; and
      a transmitter operably connected to the at least one position transducer;
   a mounting element coupled to the mounting bracket;

an electronic receiving device configured to receive the first and second signals; and a display configured to display the position and orientation of the mounting head relative to the mounting bracket.

7. An apparatus for securing and positioning a jig on a human joint, comprising:

a mounting bracket;

a first tracking marker coupled to the mounting bracket, configured to generate a first signal representative of the position and orientation in space of the mounting bracket;

a mounting head coupled to a distal end of the mounting bracket by an adjustment mechanism configured to permit six degree of freedom of movement of the mounting head relative to the mounting bracket;

position feedback means configured to generate a second signal representative of the position and orientation of the mounting head relative to the mounting bracket;

a mounting element coupled to the mounting head;

an electronic receiving device configured to receive the first and second signals; and a display configured to display the position and orientation of the mounting head relative to the mounting bracket; and further comprising at least one actuator disposed in the adjustment mechanism, the at least one actuator configured to move the mounting head relative to the mounting bracket in response to command signals.

8. An apparatus for securing and positioning a jig on a human joint, comprising:

a mounting bracket;

a first tracking marker coupled to the mounting bracket, configured to generate a first signal representative of the position and orientation in space of the mounting bracket;

a mounting head coupled to a distal end of the mounting bracket by an adjustment mechanism configured to permit six degree of freedom of movement of the mounting head relative to the mounting bracket;

position feedback means configured to generate a second signal representative of the position and orientation of the mounting head relative to the mounting bracket;

a mounting element coupled to the mounting head;

an electronic receiving device configured to receive the first and second signals; and a display configured to display the position and orientation of the mounting head relative to the mounting bracket; and further comprising a cutting block, including:

a mounting element complementary to the mounting element of the mounting head; and a guide surface configured to guide a surgical cutting instrument.

9. An apparatus for securing and positioning a jig on a human joint, comprising:

a mounting bracket;

a first tracking marker coupled to the mounting bracket, configured to generate a first signal representative of the position and orientation in space of the mounting bracket;

a mounting head coupled to a distal end of the mounting bracket by an adjustment mechanism configured to permit six degree of freedom of movement of the mounting head relative to the mounting bracket;

position feedback means configured to generate a second signal representative of the position and orientation of the mounting head relative to the mounting bracket;

a mounting element coupled to the mounting head;

an electronic receiving device configured to receive the first and second signals; and a display configured to display the position and orientation of the mounting head relative to the mounting bracket; and further comprising a drilling guide, including:

a mounting element complementary to the mounting element of the mounting head; and a plate which includes one or more guide holes.

10. An apparatus for securing and positioning a jig on a human joint, comprising:

a mounting bracket;

a first tracking marker coupled to the mounting bracket, configured to generate a first signal representative of the position and orientation in space of the mounting bracket;

a mounting head coupled to a distal end of the mounting bracket by an adjustment mechanism configured to permit six degree of freedom of movement of the mounting head relative to the mounting bracket, wherein the adjustment mechanism includes one or more adjustment knobs, each of the adjustment of configured to rotate or translate the adjustment mechanism about one axis;

position feedback means configured to generate a second signal representative of the position and orientation of the mounting head relative to the mounting bracket;

a mounting element coupled to the mounting head;

an electronic receiving device configured to receive the first and second signals; and a display configured to display the position and orientation of the mounting head relative to the mounting bracket.

11. The apparatus of claim 10, where the adjustment mechanism includes indicia indicating the position of the one or more adjustment knobs.

* * * * *